United States Patent
Chakrabarty et al.

(10) Patent No.: US 11,465,978 B2
(45) Date of Patent: Oct. 11, 2022

(54) ANTHRANILIC AMIDES AND THE USE THEREOF

(71) Applicants: THE ADMINISTRATORS OF THE TULANE EDUCATIONAL FUND, New Orleans, LA (US); DUQUESNE UNIVERSITY OF THE HOLY GHOST, Pittsburgh, PA (US)

(72) Inventors: Suravi Chakrabarty, Pittsburgh, PA (US); Patrick T. Flaherty, Pittsburgh, PA (US); Darlene Monlish, Clayton, MO (US); Jane E. Cavanaugh, Pittsburgh, PA (US); Matthew E. Burow, Slidell, LA (US); Steven Elliott, New Orleans, LA (US); Van T. Hoang, New Orleans, LA (US)

(73) Assignees: THE ADMINISTRATORS OF THE TULANE EDUCATIONAL FUND, New Orleans, LA (US); DUQUESNE UNIVERSITY OF THE HOLY GHOST, Pittsburgh, PA (US)

( * ) Notice: Subject to any disclaimer, the term of this patent is extended or adjusted under 35 U.S.C. 154(b) by 0 days.

(21) Appl. No.: 15/021,592

(22) PCT Filed: Sep. 11, 2014

(86) PCT No.: PCT/US2014/055143
§ 371 (c)(1),
(2) Date: Mar. 11, 2016

(87) PCT Pub. No.: WO2015/038743
PCT Pub. Date: Mar. 19, 2015

(65) Prior Publication Data
US 2016/0221975 A1 Aug. 4, 2016

Related U.S. Application Data

(60) Provisional application No. 61/876,645, filed on Sep. 11, 2013.

(51) Int. Cl.
| | | |
|---|---|---|
| *C07D 295/192* | (2006.01) | |
| *C07D 295/16* | (2006.01) | |
| *C07C 229/58* | (2006.01) | |
| *C07C 237/30* | (2006.01) | |
| *C07C 237/32* | (2006.01) | |
| *C07C 237/34* | (2006.01) | |
| *C07C 237/36* | (2006.01) | |

(52) U.S. Cl.
CPC .......... *C07D 295/16* (2013.01); *C07C 229/58* (2013.01); *C07C 237/30* (2013.01); *C07C 237/32* (2013.01); *C07C 237/34* (2013.01); *C07C 237/36* (2013.01)

(58) Field of Classification Search
CPC ... C07C 229/58; C07C 237/28; C07C 237/30; C07C 237/34; C07C 237/36; C07D 295/16; C07D 295/192
USPC .... 514/559, 235.8, 317, 326, 381, 524, 567; 548/418, 950; 546/210, 229; 544/392, 544/366; 562/433, 456, 454
See application file for complete search history.

(56) References Cited

U.S. PATENT DOCUMENTS

| | | | |
|---|---|---|---|
| 4,510,139 A | 4/1985 | Bailey | |
| 6,972,298 B2 * | 12/2005 | Baragi | A61K 31/165 514/382 |
| 7,019,033 B2 * | 3/2006 | Barrett | C07C 215/68 514/235.8 |
| 7,078,438 B2 * | 7/2006 | Rewcastle | C07C 259/10 514/507 |
| 9,556,112 B2 * | 1/2017 | Chakrabarty | C07C 229/58 |
| 2005/0129694 A1 | 6/2005 | Ludwig et al. | |

(Continued)

FOREIGN PATENT DOCUMENTS

| | | |
|---|---|---|
| CN | 101985428 A | 3/2011 |
| EP | 2067772 A2 | 6/2009 |

(Continued)

OTHER PUBLICATIONS

Spicer et al. J. Med. Chem. 2007, 50, 5090-5102.*

(Continued)

*Primary Examiner* — Irina Neagu
(74) *Attorney, Agent, or Firm* — F. Brent Nix, Esq.; Johnson, Marcou, Isaacs & Nix, LLC

(57) ABSTRACT

Disclosed are anthranilic amide derivatives having the formula. Compositions are disclosed that include the anthranilic amide derivatives and the use of the anthranilic amide derivatives for the manufacture of a medicament. Further disclosed are methods of inhibiting or treating cancer, inhibiting or reversing an epithelial to mesenchymal cellular transition, and/or inhibiting MEK1/2 and/or MEK 5 enzymatic activity in a subject by administering to the subject an effective amount of a disclosed anthranilic amide derivative.

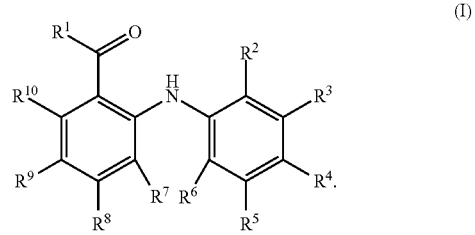

5 Claims, 19 Drawing Sheets

(56) References Cited

U.S. PATENT DOCUMENTS

| | | | |
|---|---|---|---|
| 2008/0261911 | A1 | 10/2008 | Safe et al. |
| 2009/0131527 | A1 | 5/2009 | Lee et al. |
| 2010/0137296 | A1 | 6/2010 | Attali |
| 2014/0135519 | A1* | 5/2014 | Chakrabarty ......... C07C 229/58 560/21 |
| 2016/0221975 | A1 | 8/2016 | Chakrabarty et al. |

FOREIGN PATENT DOCUMENTS

| | | | |
|---|---|---|---|
| GB | 1173540 | A | 12/1969 |
| JP | S429945 | Y1 | 5/1967 |
| JP | S5032189 | A | 3/1975 |
| JP | S5095285 | A | 7/1975 |
| JP | S5620559 | A | 2/1981 |
| JP | S5679651 | A | 6/1981 |
| JP | 2003530437 | A | 10/2003 |
| WO | 9901421 | A1 | 1/1999 |
| WO | 0040237 | A1 | 7/2000 |
| WO | WO 00/41505 | * | 7/2000 |
| WO | 0105392 | A2 | 1/2001 |
| WO | 2001056992 | A2 | 8/2001 |
| WO | 2002006213 | A2 | 1/2002 |
| WO | 03059269 | A | 7/2003 |
| WO | 03062191 | A1 | 7/2003 |
| WO | 2005030217 | A1 | 4/2005 |
| WO | 2005063254 | A2 | 7/2005 |
| WO | 2006061712 | A2 | 6/2006 |
| WO | 2008076415 | A1 | 6/2008 |
| WO | 2008132464 | A2 | 11/2008 |
| WO | 2008138639 | A1 | 11/2008 |
| WO | 2009129938 | A1 | 10/2009 |
| WO | 2012050918 | A2 | 4/2012 |
| WO | 2012171484 | A1 | 12/2012 |
| WO | 2015038743 | A1 | 3/2015 |

OTHER PUBLICATIONS

STN Registry Compound CAS No. 1354281-66-5, Entered STN: Jan. 25, 2012.*
RN 1354281-66-5, entered STN Jan. 25, 2012.*
International Search Report and Written Opinion for PCT/US2014/055143, dated Dec. 16, 2014, 21 pages.
Partial European Search Report for European Patent Application No. 14843462.4, dated Mar. 27, 2017, 9.
Andras, et al., "Relation Between the Structure of N-Phenylanthranilic Acid Derivatives and Their Antiphilogistic Effect", Acta Pharmaceutica Hungarica, Hungarian Pharmaceutical Association, vol. 43, No. 3-4, Jan. 1, 1973, 152-157.
Pontiki, et al., "Histone Deacetylase 1-15 Inhibitors (HDACIs) Structure-Activity Relationships: History and New QSAR Perspectives", Medicinal Research Reviews, vol. 31, No. 1, Jan. 16, 2012, 1-165.
Suzuki, et al., "Design Synthesis, and Biological Activity of a Novel Series of Human Sirtuin-2-Selective Inhibitors", Journal of Medicinal Chemistry, vol. 55, No. 12, Jun. 28, 2012, 5760-5773.
European Search Report and Written Opinion for European Patent Application No. 14843462.4, dated Jul. 27, 2017, 21.
Adeniji, et al., "Development of Potent and Selective Inhibitors of Aldo-Keto Reductase 1C3 (Type 5 17β3-Hydroxysteroid Dehydrogenase) Based on N-Phenyl-Aminobenzoates and Their Structure-Activity Relationships", Journal of Medicinal Chemistry, vol. 55, No. 5, Mar. 8, 2012, 2311-2323.
Barrett, et al., "The discovery of the benzhydroxamate MEK inhibitors CI-1040 and PD 0325901", Bioorganic & Medicinal Chemistry Letters, vol. 18, No. 24, Dec. 15, 2008, 6501-6504.
Bauman, et al., "Development of nonsteroidal anti-inflammatory drug analogs and steroid carboxylates selective for human aldo-keto reductase isoforms: potential antineoplastic agents that work independently of cyclooxygenase isozymes.", Molecular Pharmacology, vol. 67, No. 1, Jan. 1, 2005, 60-68.

Endo, et al., "Selective Inhibition of the Tumor Marker AKR1B10 by Antiinflammatory N-Phenylanthranilic Acids and Glycyrrhetic Acid", Biological & Pharmaceutical Bulletin, vol. 33, No. 5, Jan. 1, 2010, 886-890.
Fritzson, et al., "Inhibition of Human DHODH by 4-Hydroxycoumarins, Fenamic Acids, and N-(Alkylcarbonyl) anthranilic Acids Identified by Structure-Guided Fragment Selection", ChemMedChem, vol. 5, No. 4, Apr. 6, 2010, 608-617.
Kang, et al., "Tolfenamic Acid Induces Apoptosis and Growth Inhibition in Head and Neck Cancer: Involvement of NAG-1 Expression", PLOS One, vol. 7, No. 4, Apr. 19, 2012, e34988.
Maliakal, et al., "Chemopreventive Effects of Tolfenamic Acid Against Esophageal Tumorigenesis in Rats", The Journal of New Anticancer Agents, vol. 30, No. 3, Jan. 4, 2011, 853-861.
Oh, et al., "Development of Selective Blockers for Ca2+-activated Cl-channel Using Xenoplus Laevis Oocytes with an Improved Drug Screening Strategy", Molecular Brain, vol. 1, No. 1, Oct. 29, 2008, 14.
Penning, et al., "Aldo-keto reductase (AKR) 1C3: Role in prostate disease and the development of specific inhibitors", Molecular and Cellular Endocrinology, vol. 248, No. 1-2, Mar. 27, 2006, 182-191.
Rice, et al., "Novel Carboxamide-Based Allosteric MEK Efforts Toward XL518 (GDC-0973)", Medicinal Chemistry, vol. 3, No. 5, May 10, 2012, 416-421.
Sankpal, et al., "Small molecule tolfenamic acid inhibits PC-3 cell proliferation and invasion in vitro, and tumor growth in orthotopic mouse model for prostate cancer", Prostate, vol. 72, No. 15, Apr. 2, 2012, 1648-1658.
Suzuki, T., et al., "2-Anilinobenzamides as SIRT Inhibitors", ChemMedChem, vol. No. 1, pp. 1059-1062, 2006.
Kretschy, N., et al., "In vitro inhibition of breast cancer spheroid-induced lymphendothelial defects resembling intravasation into the lymphatic vasculature by acetohexamide, isoxsuprine, nifedipin and proadifen," British Journal of Cancer, vol. 108, No. 3, pp. 570-578, Feb. 19, 2013.
Chua, K.N., et al., "A Cell-Based Small Molecule Screening Method for Identifying Inhibitors of Epithelial-Mesenchymal Transition in Carcinoma", PLoS One (e33183), vol. No. 7, Issue No. 3, pp. 1-10, Mar. 2012.
Li, Yanqiu et al., "A One-Pot Transition-Metal-Free Tandem Process to 1,4-Benzodiazepine Scaffolds," Synthesis, vol. 45, No. 1, pp. 111-117, 2013.
MacNeil, S.L., et al., "Carbanionic Friedel-Crafts Equivalents. Regioselective Directed Ortho and Remote Metalation-C—N Cross Coupling Routes to Acridones and Dibenzo[b,f]azepinones," Journal of Organic Chemistry, vol. 73, No. 24, pp. 9710-9719, 2008.
MacNeil, S.L., et al., "Anionic N-Fries Rearrangement of N-Carbamoyl Diarylamines to Anthranilamides. Methodology and Application to Acridone and Pyranoacridone Alkaloids," Organic Letters, vol. 8, No. 6, pp. 1133-1136, 2006.
Mugrage, Ben et al., "Phosphonic acid analogs of diclofenac: an Arbuzov reaction of trimethylphosphite with an ortho-quinonoid intermediate," Tetahedron Letters, vol. 41, No. 13, pp. 2047-2050, 2000.
Mills, R.J., et al., "Directed Ortho Metalation of jV,JV-Diethylbenzamides. Silicon Protection of Ortho Sites and the o-Methyl Group," J. Org. Chem., vol. 54, No. 18, pp. 4372-4385, 1989.
Iwao, M., et al., "Directed Metalation of Tertiary Benzamides. Ortho N-Aryl Amination and Synthesis of Acridones," J. Am. Chem. Soc., vol. 104, No. 20, pp. 5531-5533, 1982.
Legrand, Louis et al., "Heterocyclic sulfur compounds. LXV. Reaction of amines with 1,2-dihydro-3,1-benzothiazin-4-one", Bulletin de la Societe Chimique de France, 1973, vol. 5 (Pt. 2), p. 9 1665-1667.
CAS RN 1389227-32-0, STN Entry Date Aug. 10, 2012, Methanone, [2-[(4-methoxyphenyl)amino]phenyl](4-methyl-1-piperazinyl)-[1].
CAS RN 1387808-46-9, STN Entry Date Aug. 8, 2012, Methanone, [4-(dimethylamino)-1-piperidinyl][2-[(4-methoxyphenyl)amino]phenyl]-.
CAS RN 1387794-34-4, STN Entry Date Aug. 8, 2012, Methanone, [4-(dimethylamino)-1-piperidinyl][2-(phenylamino)phenyl]-[1].
CAS RN 1110912-01-0, STN Entry Date Feb. 24, 2009, 1-Piperazinecarboxylic acid, 4-[2-(phenylamino)benzoyl]-, 1,1-dimethylethyl ester.

(56) References Cited

OTHER PUBLICATIONS

CAS RN 1011631-18-7, STN Entry Date Apr. 2, 2008, Methanone, [2-[(2,3- dimethylphenyl)amino]phenyl](4-methyl-1-piperazinyl)- [1].

Maliakal, P., et al., "Chemopreventive effects of tolfenamic acid against esophageal tumsrcenis in rats," Investigational New Drugs, vol. 30, No. 3-4, pp. 853-861, 2012.

Oh, Soo-Jin, et al., "Development of selective blockers for Ca2+- activated Cl-channel using Xenopus laevis oocytes with an improved drug screening strategy," Molecular Brain, 1:14, pp. 1-11, Published: Oct. 29, 2008.

Bauman, D. R., et al., "Development of Nonsteroidal Anti-Inflammatory Drug Analogs and Steroid Carboxylates Selective for Human Aldo-Keto Reductase Isoforms: Potential Antineoplastic Agents That Work Independently of Cyclooxygenase Isozymes," Molecular Pharmacology, vol. 67, No. 1, pp. 60-68, Accepted: Oct. 5, 2004.

Barrett, S.D., et al., "The discovery of the benzhydroxamate MEK inhibitors Cl-1040 and PD 0325901," Bioorganic & Medicinal Chemistry Letters, vol. 18, pp. 6501-6504, 2008.

Acta Pharmaceutica Hungarica, 1973, 43(3-4), pp. 152-157.

Chem. Abstr. (1971), vol. 74, p. 353, Abstract No. 74:42379p, "Anthranilic acid derivatives", Heterocyclic Compounds, HU 696 (19700724).

Office Action issued by the Japanese Patent Office (JPO) dated May 13, 2019 for Japanese Patent Application No. 2016-542095.

Office Action issued by the European Patent Office (EPO) dated Mar. 13, 2020 for European Patent Application No. 14843462.4.

Vedres, et al., "Anthranilic acid derivatives", Chemical Abstract from HU696U, American Chemical Society, Jul. 24, 1970.

"Office Action", issued by the Canadian Intellectual Patent Office (CIPO) for counterpart Canadian application No. 2,923,835 dated Oct. 15, 2020.

"Office Action", issued by the Japanese Patent Office for counterpart application No. 2016-542095 dated Sep. 23, 2020.

"Reconsideration Report by Examiner before Appeal", Appeal or Trial No. Appeal 2019-012182, Japanese Patent Application No. 2016-542095, pp. 1-9, issued by the Japanese Patent Office dated Feb. 18, 2020.

"Decision by the Board of Appeals to Grant Patent" issued by the Japanese Patent Office for counterpart Application No. JP 2016- 542095 dated Mar. 8, 2021.

"Office Action issued by the Canadian Patent Office (CIPO)", for counterpart application No. 2,923,835 dated Apr. 26, 2021.

"Decision to grant a European Patent pursuant to Article 97(1) EPC" for counterpart Application No. EP 14843462.4 by The European Patent Office dated Apr. 30, 2021.

"Notice of Allowance" issued by the Canadian Patent Office for counterpart Application No. CA 2,923,835 dated Apr. 12, 2022.

Hoang, et al., "MEK5-ERK5 Signaling in Cancer: Implications for Targeted Therapy", Cancer Lett., vol. 392, pp. 51-59, Published: Apr. 28, 2017.

Stecca, et al., "Impact of ERK5 on the Hallmarks of Cancer", International Journal of Molecular Sciences, vol. 20, No. 1426, pp. 1-21, Published: Mar. 21, 2019.

* cited by examiner

I: Side chain variations
• Modify solubility
• Examine MEK-5 predicted interactions II: Amide ariations III: Central arene IV: Terminal arene. Goals:
• Minimal necessary substitution
• MEK-5 selective interactions Scheme 1: Synthesis of compounds 9a-j via acid chloride

Scheme 2: Synthesis of compound 15 by EDCI coupling

FIG. 7 Scheme 4: Synthesis of compounds 23, 24 via acid chloride

FIG. 9
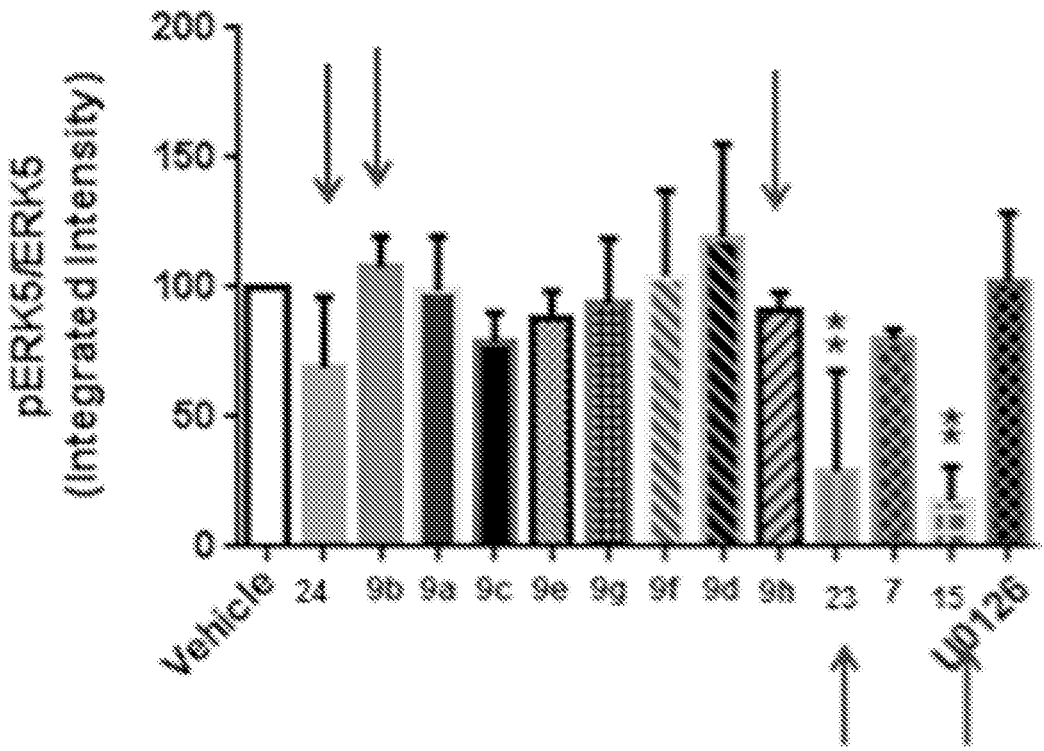
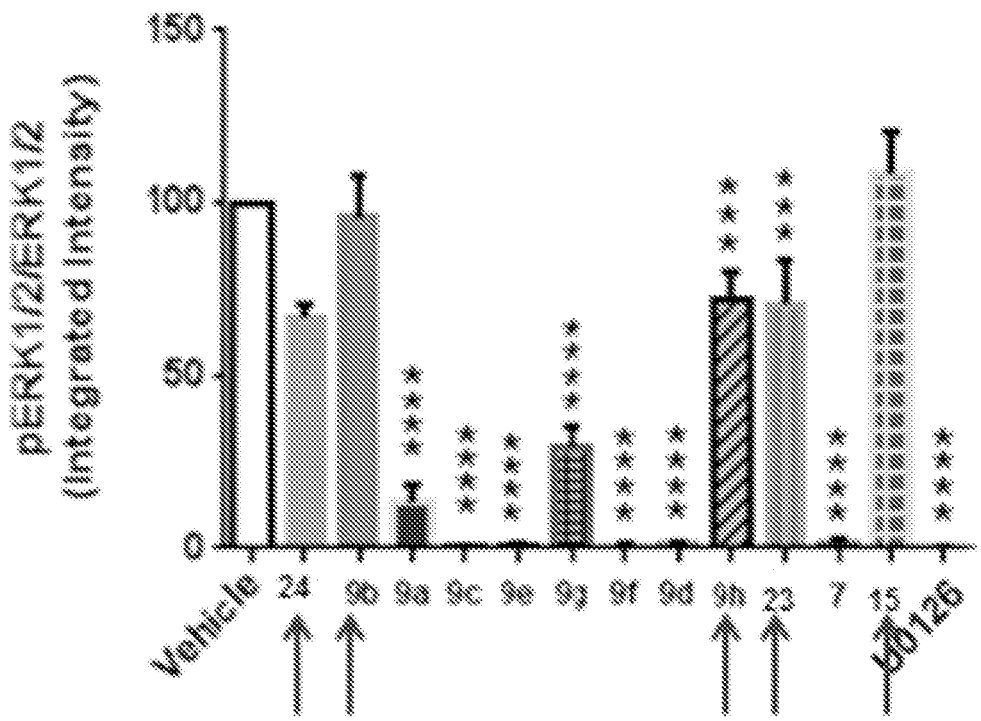

FIG. 10

| Compounds | pERK-5 relative activity (%) | pERK-5 decrease (%) | pERK-1/2 relative activity (%) | pERK-1/2 decrease (%) |
|---|---|---|---|---|
| Vehicle | 100 | 0 | 100 | 0 |
| 24 | --- | 30.9 | --- | 33.1 |
| 9b | 107.9 | Activation | --- | 4.4 |
| 9h | --- | 9 | --- | 28.2 |
| 23 | --- | 71 | --- | 29.3 |
| 7 | --- | 20.1 | --- | 98.52 |
| 15 | --- | 82.4 | 108.5 | --- |
| U0126 | 102.1 | --- | 0.28 | 99.72 |

FIG. 12
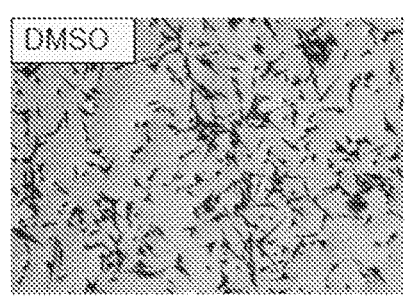
Blank (DMSO) treated MDA-MB 231 cells
t= Day 7
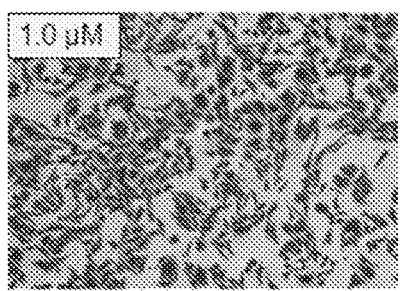 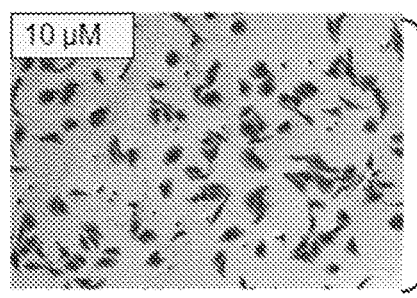
Compound 3 treated
MDA-MB 231 cells
t= Day 7

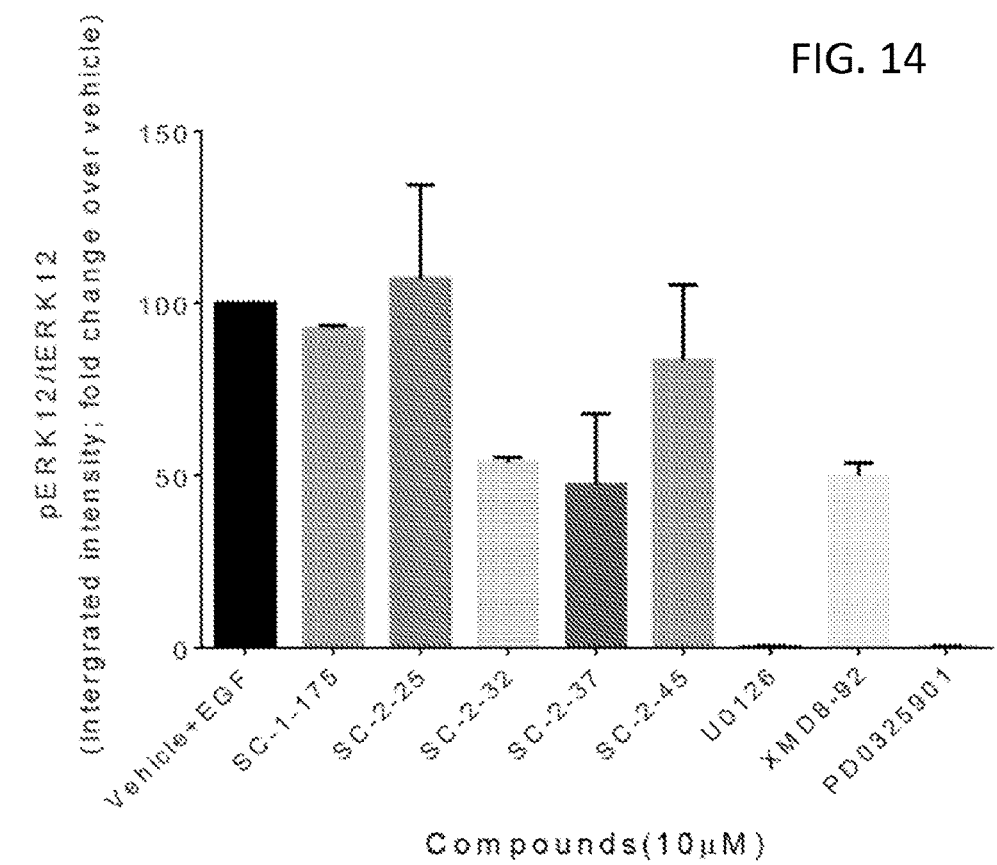
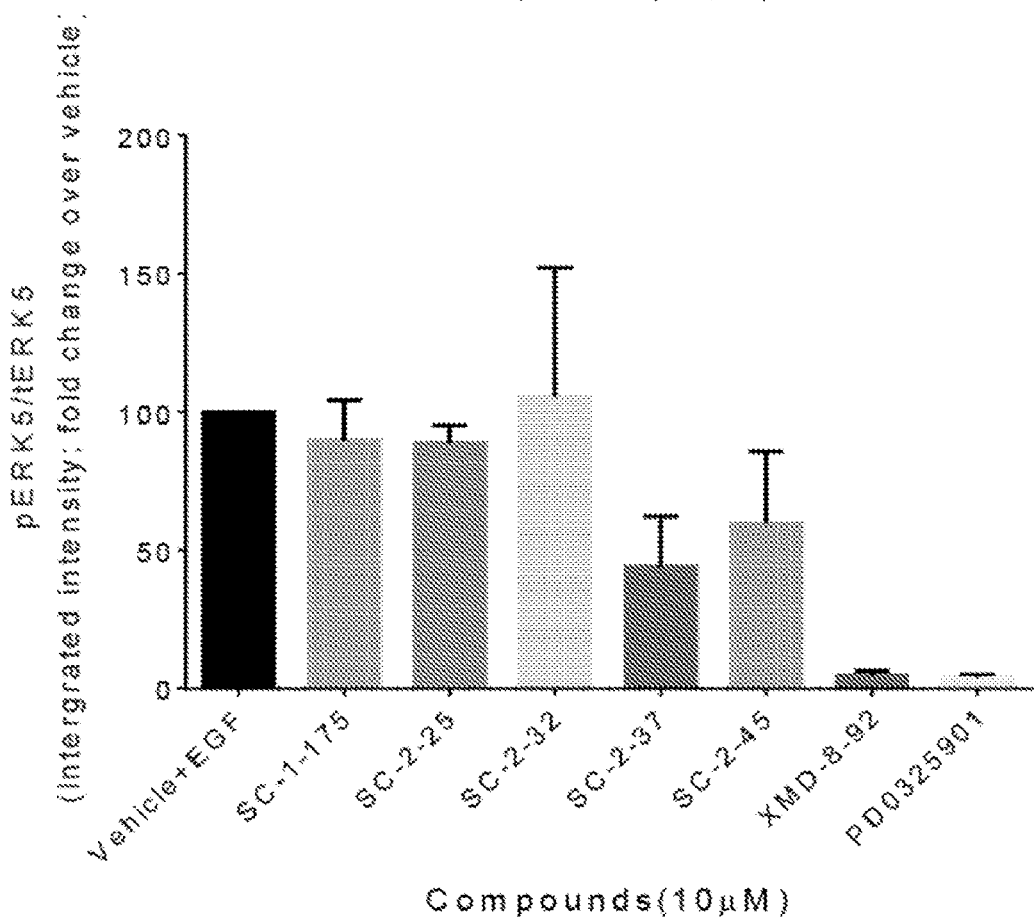
FIG. 14

ANTHRANILIC AMIDES AND THE USE THEREOF

CROSS-REFERENCE TO RELATED APPLICATION

This application is a 35 U.S.C. 371 national stage application of International Application No. PCT/US2014/055143 filed on Sep. 11, 2014, published in English under PCT Article 21(2), which claims the benefit of priority to U.S. Provisional Application No. 61/876,645, filed on Sep. 11, 2013, the disclosures of which are specifically incorporated by reference herein in their entirety.

ACKNOWLEDGMENT OF GOVERNMENT SUPPORT

This invention was made with government support under grant numbers R01 CA125806 and R15 CA176496 awarded by the National Institutes of Health. The government has certain rights in the invention.

FIELD

The present invention relates to anthranilic amide compounds useful for the inhibition of MEK kinases, such as MEK5 and/or MEK1/2, for example in the treatment of various cancer types.

BACKGROUND

Cancer is the second leading cause of death in the United States, only exceeded by heart disease. Cancer is characterized by uncontrolled proliferation and systemic dissemination of tumor cells as a result of dys-regulation of cellular pathways that control normal biological functioning. Mitogen-Activated Protein Kinases (MAPK) are a family of protein-serine/threonine kinases. These kinases are major components of pathways that control embryogenesis, cell differentiation, cell proliferation, and cell death. Cellular responses to a wide variety of stimuli, including mitogens, osmotic stress, heat shock and proinflammatory cytokines, are directed by MAPKs. The activation of MAPKs requires complicated intersecting signaling cascades triggering phosphorylation events. The MAPK pathway involves a phosphorylation cascade where a MAP kinase kinase (MEKK) phosphorylates the subsequent MAP kinase kinase (MEK), which then phosphorylates the next downstream kinase MAP kinase (ERK).

The MEK5 signaling pathway allows cells to survive oxidative stress and can be activated by mitogens (EGF and G-CSF), cytokines (LIF and CT-1), and stress ($H_2O_2$ and sorbitol). ERK5 is the only known substrate of MEK5, and it is phosphorylated at Thr and Tyr residues within the Thr-Glu-Tyr (TEY) activation motif ERK5 has a role facilitating the G1/S cell-cycle transition for EGF-induced cell proliferation via a cAMP response element (CRE). ERK5 is significantly up-regulated in response to stressors, including radiation, palyotoxin, and phorbol ester treatment. Studies show that MEK5 is overexpressed in 50% of tumors and other cancers; it is significantly up-regulated in squamous cell carcinoma, prostate and early and triple-negative breast cancers. MEK5 has approximately 87% homology of the ATP binding pocket with MEK1.

The inter-conversion of epithelial and mesenchymal cell morphology is an important process occurring during embryonic development, and it is believed to be reactive during cancer development. Cells with an epithelial-like morphology lack motility and are more tightly packed whereas cells that exhibit a mesenchymal morphology are more fibroblastoid or spindle-shaped and exhibit high motility.

Various signaling pathways, including MEK/ERK pathways, are significantly up-regulated in certain cancer types and are thought to play a role in the transition to a more invasive phenotype. Small molecules that modify the conversion of cell types with an EMT (epithelial to mesenchymal) or a MET (mesenchymal to epithelial) transition are increasingly being sought in the context of cancer therapy to establish a more homogenous population of cancer cells to optimize current therapy and to prevent conversion of cancer cells to a more aggressively dividing and invasive phenotype.

SUMMARY

Disclosed are anthranilic amide derivatives having the formula:

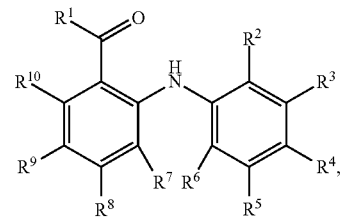

wherein $R_1$ independently is:

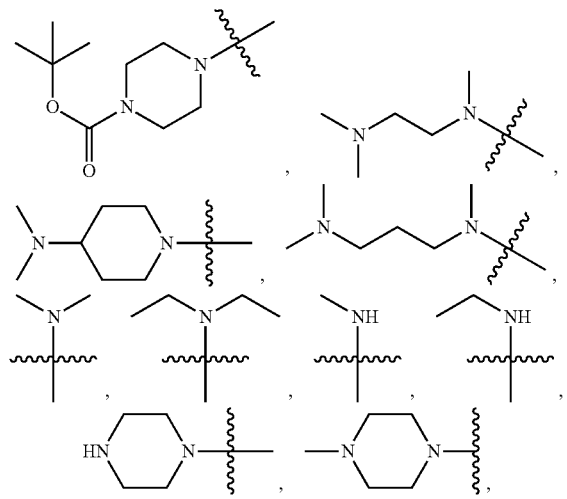

a primary or tertiary amine, $OR_{11}$, or a amino acid, and wherein the Ru independently is hydrogen, alkyl, alkene, alkyne; and $R_2$, $R_3$, $R_4$, $R_5$, $R_6$, $R_7$, $R_8$, $R_9$, and $R_{10}$ are each independently hydrogen, alkyl, alkene, alkyne, halogen, such as one of fluorine, chlorine, bromine, or iodine, alkoxy, such as a $C_1$-$C_4$ with or without more or more carbon-carbon double or triple bonds, cyano group, or nitrile group. In specific examples an anthranilic amide derivative is one of 3,4-difluoro-2-((2-fluoro-4-iodophenyl)amino)benzoic acid (SC-1-180), 3,4-difluoro-2-((2-fluoro-4-iodophenyl)amino) benzamide (SC-1-151 primary amide), N,N-diethyl-3,4-difluoro-2-((2-fluoro-4-iodophenyl)amino)benzamide (SC-1-65), 3,4-difluoro-2-((2-fluoro-4-iodophenyl)amino)-N,N-dimethylbenzamide (SC-1-69), 3,4-difluoro-2-((2-fluoro-4-iodophenyl)amino)-N-methylbenzamide (SC-1-72 amide), Methyl 3,4-difluoro-2-((2-fluoro-4-iodophenyl)amino)benzoate (SC-1-72 ester), Tert-butyl 4-(3,4-difluoro-2-((2-fluoro-4-iodophenyl)amino)benzoyl)piperazine-1-carboxylate (SC-1-75), (3,4-difluoro-2-((2-fluoro-4-iodophenyl)amino)phenyl)(piperazin-1-yl)methanone, hydrochloride (SC-1-79), N-ethyl-3,4-difluoro-2-((2-fluoro-4-iodophenyl)amino)benzamide (SC-1-80), N-(2-(dimethylamino)ethyl)-3,4-difluoro-2-((2-fluoro-4-iodophenyl)amino)-Nmethyl-benzamide hydrochloride (SC-1-122), 2-((2-fluoro-4-iodophenyl)amino)benzoic acid (SC-1-14 acid), (2-((2-fluoro-4-iodophenyl)amino)phenyl)(4-methylpiperazin-1-yl)methanone hydrochloride (SC-1-24 amide), 2-(phenylamino)benzoic acid (SC-1-39 acid), (4-methylpiperazin-1-yl)(2-(phenylamino)phenyl)methanone (SC-1-177 amide), 3,4-difluoro-2-(phenylamino)benzoic acid (SC-1-175 acid), 3,4-difluoro-2-(phenylamino)phenyl)(4-methylpiperazin-1-yl)methanone (SC-1-181), 3,4-difluoro-2-((2-fluorophenyl)amino)benzoic acid (SC-2-25 acid), (3,4-difluoro-2-((2-fluorophenyl)amino)phenyl)(4-methylpiperazin-1-yl)methanone mono-fumarate (SC-2-45), 3,4-difluoro-2-((2-fluorophenyl)amino)benzamide (SC-2-37), or 3,4-difluoro-2-((2-fluoro-4-iodophenyl)(methyl)amino)benzoic acid (SC-2-32 acid).

Also disclosed are composition, such as pharmaceutical compositions that include the anthranilic amide derivatives and the use of the anthranilic amide derivatives for the manufacture of a medicament.

Also disclosed is a method of inhibiting or treating cancer in a subject. The disclosed method includes administering to the subject an effective amount of a disclosed anthranilic amide derivative, thereby inhibiting or treating cancer. In some examples, the cancer comprises a solid tumor, such as a squamous cell carcinoma, prostate cancer, breast cancer or pancreatic cancer. In some examples, the cancer comprises metastatic cancer.

Also disclosed is a method of inhibiting or reversing an epithelial to mesenchymal cellular transition a subject. The method includes administering to the subject an effective amount of a disclosed anthranilic amide derivative, thereby inhibiting or reversing the epithelial to mesenchymal cellular transition.

Also disclosed is a method of inhibiting MEK1/2 and/or MEK 5 enzymatic activity in a subject. The method includes administering to the subject an effective amount of a disclosed anthranilic amide derivative, thereby inhibiting MEK1/2 and/or MEK 5 enzymatic activity.

The foregoing and other features, and advantages of this disclosure will become more apparent from the following detailed description, which proceeds with reference to the accompanying figures.

BRIEF DESCRIPTION OF THE DRAWINGS

FIG. 9 is a set of bar graphs showing a Western blot analysis of potential MEK5 inhibitors. The MDA-MB-231 triple negative breast cancer cell line was pretreated with compounds (10 μM) for 30 minutes followed by stimulation with epidermal growth factor (EGF, 50 ng/mL) for 15 minutes. Vehicle-treated cells were pretreated with DMSO for 30 minutes prior to EGF stimulation for 15 minutes. Protein visualization and quantification analysis were performed using LI-COR Odyssey Imager. * $P<0.05$ vs. Vehicle, one-way ANOVA followed by Tukey-Kramer test (n=3).

FIG. 10 is a table showing the results of a cellular assay of inhibition of EGF-mediated formation of pERK isoforms.

FIG. 12 is a set of digital images illustrating the conversion of cells treated with Compound 3 from an elongated, spiky cellular morphology, characteristic of the mobile and invasive mesenchymal phenotype, to a more rounded cellular morphology, characteristic of a less mobile, less invasive epithelial phenotype.

FIG. 14 is a set of bar graphs illustrating the results of the tests in Example 3.

DETAILED DESCRIPTION OF SEVERAL EMBODIMENTS

I. Summary of Terms

Figure 1:
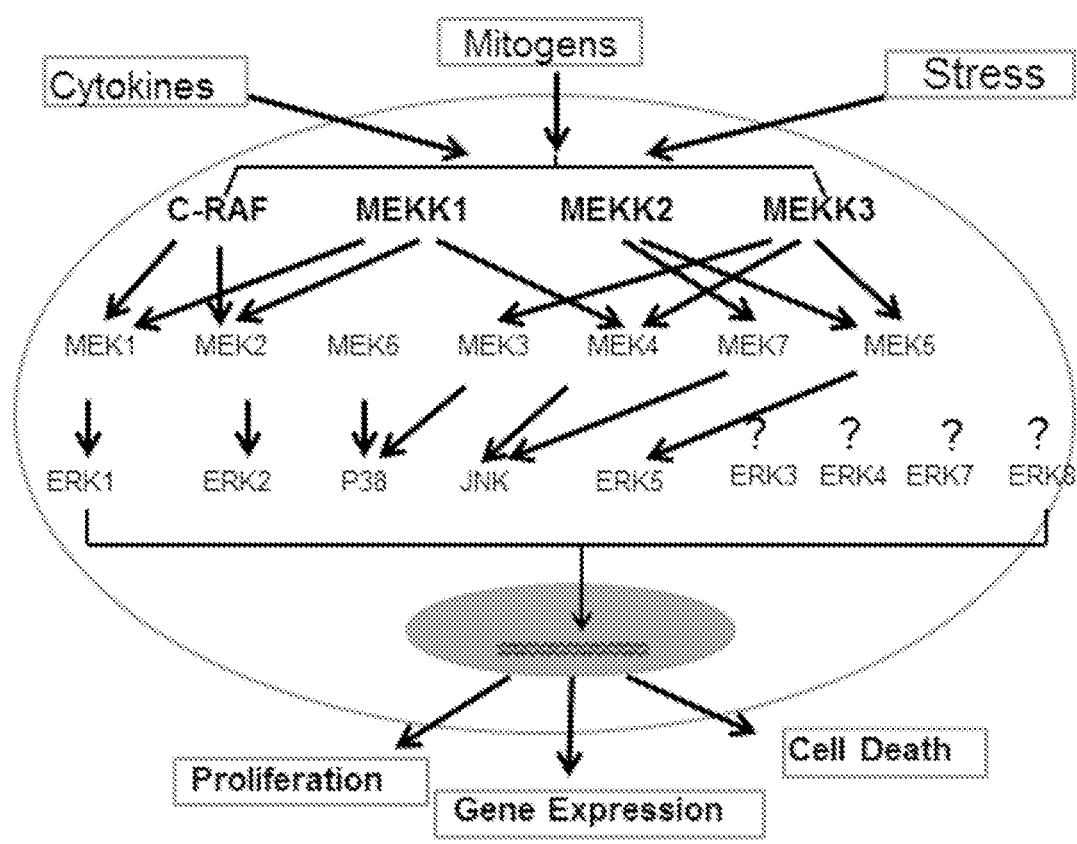
FIG. 1 is a diagram of the MAPK signaling pathways.

Unless otherwise explained, all technical and scientific terms used herein have the same meaning as commonly understood by one of ordinary skill in the art to which the disclosed subject matter belongs. Definitions of common terms in chemistry terms may be found in The McGraw-Hill Dictionary of Chemical Terms, 1985, and The Condensed Chemical Dictionary, 1981. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references. As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. Except as otherwise noted, any quantitative values are approximate whether the word "about" or "approximately" or the like are stated or not. The materials, methods, and examples described herein are illustrative only and not intended to be limiting. Any molecular weight or molecular mass values are approximate and are provided only for description. Except as otherwise noted, the methods and techniques of the present invention are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

In case of conflict, the present specification, including explanations of terms, will control.

To facilitate review of the various embodiments of this disclosure, the following explanations of specific terms are provided:

Administration: To provide or give a subject a composition, such as a pharmaceutical composition including a disclosed anthranilic amide derivative, by any effective route. Exemplary routes of administration include, but are not limited to, injection (such as subcutaneous, intramuscular, intradermal, intraperitoneal (ip), and intravenous (iv)), oral, sublingual, transdermal, and inhalation routes.

Alkoxy: A radical (or substituent) having the structure —O—R, where R is a substituted or unsubstituted alkyl. Methoxy (—OCH$_3$) is an exemplary alkoxy group. In a substituted alkoxy, R is alkyl substituted with a non-interfering substituent. "Thioalkoxy" refers to —S—R, where R is substituted or unsubstituted alkyl. "Haloalkyloxy" means a radical —OR where R is a haloalkyl. In some examples a alkoxy group is a $C_1$-$C_8$ alkoxy. In some examples an alkoxy group is a $C_1$-$C_4$ alkoxy. In some examples an alkoxy group is a methoxy.

Alkenyl: A unsaturated monovalent hydrocarbon having a number of carbon atoms ranging from one to ten (e.g., $C_{2-10}$alkenyl) from one to six, or from one to four carbon atoms, which has at least one carbon-carbon double bond and is derived from removing one hydrogen atom from one carbon atom of a parent alkene. An alkenyl group may be branched, straight-chain, cyclic, cis, or trans (e.g., E or Z). In some examples an alkenyl is a $C_{2-4}$alkenyl.

Alkynyl: A unsaturated monovalent hydrocarbon having a number of carbon atoms ranging from one to ten (e.g., $C_{2-10}$alkynyl) such as from one to six, or from one to four carbon atoms, which has at least one carbon-carbon triple bond and is derived from removing hydrogen atoms from one carbon atom of a parent alkyne. An alkynyl group may be branched, straight-chain, or cyclic. In some examples an alkenyl is a $C_{2-4}$alkynyl.

Alkyl: An acyclic, saturated, branched- or straight-chain hydrocarbon radical, which, unless expressly stated otherwise, contains from one to fifteen carbon atoms; for example, from one to ten, from one to six, or from one to four carbon atoms. This term includes, for example, groups such as methyl, ethyl, n-propyl, isopropyl, isobutyl, t-butyl, pentyl, heptyl, octyl, nonyl, decyl, or dodecyl. The term "lower alkyl" refers to an alkyl group containing from one to four carbon atoms. Unless expressly referred to as an "unsubstituted alkyl," alkyl groups can either be unsubstituted or substituted. An alkyl group can be substituted with one or more substituents (for example, up to two substituents for each methylene carbon in an alkyl chain). Exemplary alkyl substituents include, for instance, amino groups, amide, sulfonamide, halogen, cyano, carboxy, hydroxy, mercapto, trifluoromethyl, alkyl, alkoxy (such as methoxy), alkylthio, thioalkoxy, arylalkyl, heteroaryl, alkylamino, dialkylamino, alkylsulfano, keto, or other functionality.

Anti-proliferative activity: An activity of a molecule, for example a small molecule, such as a disclosed anthranilic amide derivative, which reduces proliferation of at least one cell type, but which may reduce the proliferation (either in absolute terms or in rate terms) of multiple different cell types (e.g., different cell lines, different species, etc.). In specific embodiments, anti-proliferative activity of a disclosed anthranilic amide derivative will be apparent against cells obtained from a subject diagnosed with cancer, such as a solid tumor.

Anti-cell motility or cell invasion activity: An activity of a molecule, for example, a small molecule, such as a disclosed anthranilic amide derivative, which reduces cell motility or cell invasion through an extracellular matrix (ECM), such as a disclosed anthranilic amide derivative, in at least one cell type, but may reduce the motility or invasion (either in absolute terms or in rate terms) or multiple different cell types (e.g. different cell lines, different species, etc.). In specific embodiments, anti-cell motility or anti-cell invasion activity of Matrigel will be apparent against cells obtained from a subject diagnosed with cancer, such as a solid tumor.

Epithelial-mesenchymal transition (EMT): A process by which epithelial cells lose their cell polarity and cell-cell adhesion, and gain migratory and invasive properties to become mesenchymal cells. EMT has been shown to occur in the initiation of metastasis for cancer progression. In some examples a disclosed a disclosed anthranilic amide derivative acts as an inhibitor of the EMT transition.

Biological signaling pathway: A systems of proteins, such as tyrosine kinases, and other molecules that act in an orchestrated fashion to mediate the response of a cell toward internal and external signals. In some examples, biological signaling pathways include the MEK/ERK pathway. In some examples a disclosed a disclosed anthranilic amide derivative acts as an inhibitor of the MEK/ERK pathway.

Cancer: A malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia, and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer (such as adenocarcinoma), lung cancers, gynecological cancers (such as, cancers of the uterus (e.g., endometrial carcinoma), cervix (e.g., cervical carcinoma, pre-tumor cervical dysplasia), ovaries (e.g., ovarian carcinoma, serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, malignant teratoma), vulva (e.g., squamous cell carcinoma, intraepithelial carcinoma, adenocarcinoma, fibrosarcoma, melanoma), vagina (e.g., clear cell carcinoma, squamous cell carcinoma, botryoid sarcoma), embryonal rhabdomyosarcoma, and fallopian tubes (e.g., carcinoma)), prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma), and skin cancer (such as melanoma and non-melanoma).

Cell motility: The ability of cells to move, characterized by formation of cellular projections and re-organization of the actinomyosin cytoskeleton. There are various methods of determining cell proliferation known to those of skill in the art.

Cell invasion: The ability of cells to invade through an extracellular matrix substrate (such as Matrigel, laminin, collagen, etc.), characterized by formation of lamelliopodia and the activation of matrix remodeling and destruction proteins, including matrix metalloproteinases (MMPs). Local cell invasion is the first step in the metastatic cascade. There are various methods of determining cell invasion known to those of skill in the art.

Cell proliferation: The ability of cells to multiply, for example through rounds of cell division. There are various methods of determining cell proliferation known to those of skill in the art.

Chemotherapy: In cancer treatment, chemotherapy refers to the administration of one or more agents (chemotherapeutic agents) to kill or slow the reproduction of rapidly multiplying cells, such as tumor or cancer cells. In a particular example, chemotherapy refers to the administration of one or more agents to significantly reduce the number of tumor cells in the subject, such as by at least about 50% (the IC50 dose). "Chemotherapeutic agents" include any chemical agent with therapeutic usefulness in the treatment of cancer.

Examples of chemotherapeutic agents can be found for example in Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy Handbook, 4th ed. St. Louis, Mosby-Year Book, 1993). A chemotherapeutic agent of use in a subject, such as a the MEK/ERK pathway inhibitor, such as a disclosed anthranilic amide derivative, can decrease a sign or a symptom of a cancer, or can reduce, stop or reverse the progression, metastasis and/or growth of a cancer.

Contacting: Placement in direct physical association including both in solid or liquid form. Contacting can occur in vivo, for example by administering an agent to a subject.

Diagnostic: Identifying the presence or nature of a pathologic condition, such as cancer, such as metastatic breast cancer. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (for example severity) of a pathologic condition.

Inhibiting or treating a disease: Inhibiting the full development of a disease or condition, for example, in a subject who is at risk for a disease such cancer, for example a solid tumor. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other clinical or physiological parameters associated with a particular disease. A "prophylactic" treatment is a treatment administered to a subject who does not exhibit signs of a disease or exhibits only early signs for the purpose of decreasing the risk of developing pathology.

Inhibit: To reduce to a measurable extent. For example, to reduce enzymatic activity or to inhibit cell proliferation, motility or invasion. In some examples, the enzymatic activity of MEK1/2 and/or MEK5 is inhibited, for example, using a small molecule inhibitor of MEK1/2 and/or MEK5, such as a disclosed anthranilic amide derivative.

Kinase: An enzyme that catalyzes the transfer of a phosphate group from one molecule to another. Kinases play a role in the regulation of cell proliferation and survival, differentiation, metabolism, motility, migration, and invasion. In some examples, a kinase is MEK1/2 and/or MEK5.

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the compositions disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Prognosis: The probable course or outcome of a disease process. In several examples, the prognosis of a subject with cancer can indicate the likelihood of survival, the likelihood of relapse-free survival and/or the likelihood of overall survival. The prognosis of a subject with cancer can indicate the likelihood that the subject will survive for a period of time, such as about one, about two, about three, about four, about five or about ten years. The prognosis of a subject with cancer can also indicate the likelihood of a cure, of the likelihood that the subject will remain disease-free following treatment for a period of time, such as about one, about two, about three, about four, about five or about ten years.

Small molecule: A molecule, typically with a molecular weight less than about 1000 Daltons, or in some embodiments, less than about 500 Daltons, wherein the molecule is capable of modulating, to some measurable extent, an activity of a target molecule such as inhibiting the activity of a tyrosine kinase. In some examples, a small molecule is a disclosed anthranilic amide derivative.

Subject: The term "subject" includes both human and veterinary subjects, for example, humans, non-human primates, dogs, cats, horses, rats, mice, and cows. Similarly, the term mammal includes both human and non-human mammals.

Therapeutic agent: A chemical compound, small molecule, or other composition capable of inducing a desired therapeutic or prophylactic effect when properly administered to a subject.

Therapeutically effective amount or Effective amount: The amount of agent, such as a chemotherapeutic agent, such as a disclosed anthranilic amide derivative, that is sufficient to prevent, treat (including prophylaxis), reduce and/or ameliorate the symptoms and/or underlying causes of any of a disorder or disease, for example to prevent, inhibit, and/or treat cancer.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999; Harlow and Lane, Antibodies: A Laboratory Manual, Cold Spring Harbor Laboratory Press, 1990; and Harlow and Lane, Using Antibodies: A Laboratory Manual, Cold Spring Harbor Laboratory Press, 1999. In addition, the materials, methods, and examples are illustrative only and not intended to be limiting.

II. Description of Several Embodiments

A. Introduction

Mitogen-Activated Protein Kinases (MAPK) are a family of protein-serine/threonine kinases. These kinases are major components of pathways that control embryogenesis, cell differentiation, cell proliferation, and cell death. The MEK5 signaling pathway allows cells to survive oxidative stress and can be activated by mitogens (EGF and G-CSF), cytokines (LIF and CT-1), and stress ($H_2O_2$ and sorbitol). Various signaling pathways, including MEK/ERK pathways, are significantly up-regulated in certain cancer types and are thought to play a role in the transition to a more invasive mesenchymal phenotype.

In recent years, there has been a growing body of literature that addresses MEK1/2 inhibitors, yet there is a lack of selective inhibitors of the enzyme MEK5. MEK1/2 inhibitors were initially designed to mimic the triphosphate tail of ATP and to extend from a hydrophobic pocket close to, but different from, the ATP binding pocket. Subsequent work showed that the MEK1/2 inhibitors bound to this hydrophobic pocket but did not mimic the triphosphate tail of ATP. As a result, these compounds did not display competitive binding with ATP. This class of inhibitors is currently termed type III inhibitors.

Using a rational drug design approach, compounds were designed to selectively inhibit MEK5. A computer model for MEK5 was built, as there is not an availed x-ray crystal structure of MEK5 in the PDB database. The derivative design strategy explored the substations on the aryl rings and the substitutions on the acyl group to map out non-tolerated, tolerated, and activity increasing substitutions. Initially, approximately 70 specific compounds were prepared as representative examples of the MEK5 and/or MEK1/2 inhibitors disclosed herein. Structures of representative anthranilic amide derivatives are provided below in Table 1. These compounds displayed differential inhibition of MEK5 and/or MEK1/2 and were tested for inhibition of cancer cell proliferation. Additionally, some compounds selectively reversed the mesenchymal phenotype back to a more epithelial phenotype. Reversal of the phenotype is useful in the treatment or prevention of cancers. Although there has been some exploration for compounds that can block or prevent the conversion of epithelial cells to a mesenchymal phenotype, there have been no small molecule compounds in the literature that can reverse cells with a mesenchymal phenotype to a normal epithelial phenotype.

The novel anthranilic amide derivatives disclosed herein provide compositions and methods of treatment and/or prevention for various cancers and may also provide methods of treatment and/or prevention for other diseases which involve or implicate the MEK1/2 and/or MEK5 signaling pathways. In addition, the disclosed anthranilic amide derivative compounds can be used for in vitro studies, for example as models of MEK1/2 and/or MEK 5 inhibition, such as to test the ability of other inhibitors to inhibit these enzymes, both in cellular and non-cellular systems, such as enzymatic assays. Thus, all of the disclosed compounds have substantial utility.

B. Anthranilic Amide Derivatives

Disclosed are compounds, collectively referred to herein as anthranilic amide derivatives, that may be used as for the treatment of cancer, such as solid tumors, for example breast cancer, pancreatic cancer, squamous cell carcinoma, prostate and/or early and triple-negative breast cancers. The compounds are particularly effective in blocking, preventing and/or reversing the epithelial to mesenchymal transition, for example during cancer progression and in particular cancer metastasis. Other uses for the compounds include reducing the expression of epithelial to mesenchymal (EMT) genes as well is in vitro and in vivo assays as described below. In specific examples, the compound is a small-molecule therapeutic.

In particular disclosed embodiments, an anthranilic amide derivative is a multi cyclic compound of the formula illustrated below:

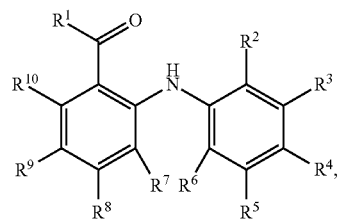

Formula I wherein $R_1$ independently is:

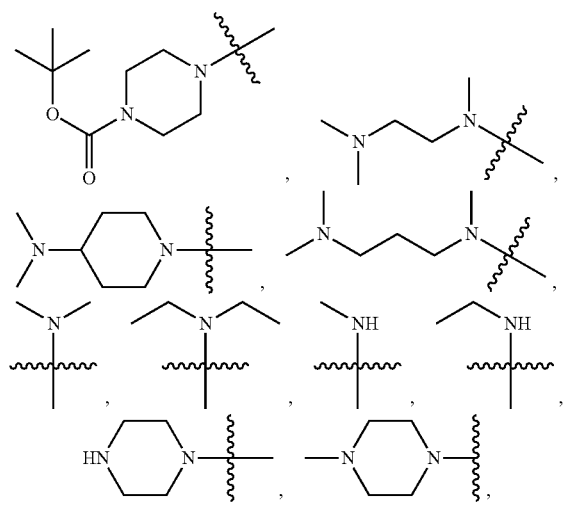

a primary or tertiary amine, $OR_{11}$, or a amino acid, and wherein $R_{11}$ independently is hydrogen, alkyl, alkenyl, alkenyl; $R_2$ independently is hydrogen, alkyl, alkenyl, alkenyl, halogen, such as one of fluorine, chlorine, bromine, or iodine, alkoxy, such as a $C_1$-$C_4$ with or without one or more carbon-carbon double or triple bonds, cyano group, or nitrile group; $R_3$ independently is hydrogen, alkyl, alkenyl, alkenyl, halogen, such as one of fluorine, chlorine, bromine, or iodine, alkoxy, such as a $C_1$-$C_4$ with or without more or more carbon-carbon double or triple bonds, cyano group, or nitrile group; $R_4$ independently is hydrogen, alkyl, alkenyl, alkenyl, halogen, such as one of fluorine, chlorine, bromine, or iodine, alkoxy, such as a $C_1$-$C_4$ with or without more or more carbon-carbon double or triple bonds, cyano group, or nitrile group; $R_5$ independently is hydrogen, alkyl, alkenyl, alkenyl, halogen, such as one of fluorine, chlorine, bromine, or iodine, alkoxy, such as a $C_1$-$C_4$ with or without more or more carbon-carbon double or triple bonds, cyano group, or nitrile group; $R_6$ independently is hydrogen, alkyl, alkenyl, alkenyl, halogen, such as one of fluorine, chlorine, bromine, or iodine, alkoxy, such as a $C_1$-$C_4$ with or without more or more carbon-carbon double or triple bonds, cyano group, or nitrile group; $R_7$ independently is hydrogen, alkyl, alkenyl, alkenyl, halogen, such as one of fluorine, chlorine, bromine, or iodine, alkoxy, such as a $C_1$-$C_4$ with or without more or more carbon-carbon double or triple bonds, cyano group, or nitrile group; $R_8$ independently is hydrogen, alkyl, alkenyl, alkenyl, halogen, such as one of fluorine, chlorine, bromine, or iodine, alkoxy, such as a $C_1$-$C_4$ with or without more or more carbon-carbon double or triple bonds, cyano group, or nitrile group; $R_9$ independently is hydrogen, alkyl, alkenyl, alkenyl, halogen, such as one of fluorine, chlorine, bromine, or iodine, alkoxy, such as a $C_1$-$C_4$ with or without more or more carbon-carbon double or triple bonds, cyano group, or nitrile group; and $R_9$ independently is hydrogen, alkyl, alkenyl, alkenyl, halogen, such as one of fluorine, chlorine, bromine, or iodine, alkoxy, such as a $C_1$-$C_4$ with or without more or more carbon-carbon double or triple bonds, cyano group, or nitrile group. It will be readily apparent to one of ordinary skill in the art that any substituent of any or all of the R groups described above can be selected in any combination or sub-combination.

In some embodiments, $R_2$ is hydrogen. In some embodiments, $R_2$ is halogen, such as one of fluorine, chlorine, bromine, or iodine. In some embodiments, $R_2$ is flourine.

In some embodiments, $R_3$ is hydrogen. In some embodiments, $R_3$ is halogen, such as one of fluorine, chlorine, bromine, or iodine.

In some embodiments, $R_4$ is hydrogen. In some embodiments, $R_4$ is halogen, such as one of fluorine, chlorine, bromine, or iodine. In some embodiments, $R_4$ is iodine.

In some embodiments, $R_5$ is hydrogen. In some embodiments, $R_5$ is halogen, such as one of fluorine, chlorine, bromine, or iodine.

In some embodiments, $R_6$ is hydrogen. In some embodiments, $R_6$ is halogen, such as one of fluorine, chlorine, bromine, or iodine. In some embodiments, $R_6$ is fluorine.

In some embodiments, $R_7$ is hydrogen. In some embodiments, $R_7$ is halogen, such as one of fluorine, chlorine, bromine, or iodine. In some embodiments, $R_7$ is fluorine.

In some embodiments, $R_8$ is hydrogen. In some embodiments, $R_8$ is halogen, such as one of fluorine, chlorine, bromine, or iodine.

In some embodiments, $R_9$ is hydrogen. In some embodiments, $R_9$ is halogen, such as one of fluorine, chlorine, bromine, or iodine.

In some embodiments, $R_{10}$ is hydrogen. In some embodiments, $R_{10}$ is halogen, such as one of fluorine, chlorine, bromine, or iodine.

In particular disclosed embodiments, a disclosed anthranilic amide derivative has the formula illustrated below:

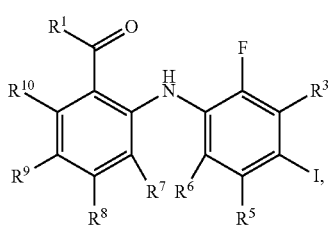

Formula II wherein the R groups are defined as above with respect to Formula I.

In particular disclosed embodiments, a disclosed anthranilic amide derivative has the formula illustrated below:

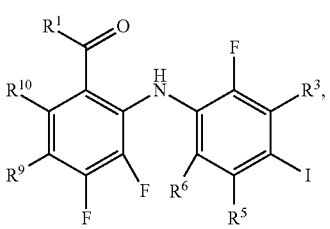

Formula III wherein the R groups are defined as above with respect to Formula I.

In particular disclosed embodiments, a disclosed anthranilic amide derivative has the formula illustrated below:

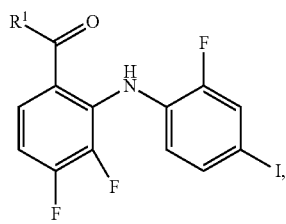

Formula IV wherein the R group is defined as above with respect to Formula I.

In particular disclosed embodiments, a disclosed anthranilic amide derivative has the formula illustrated below:

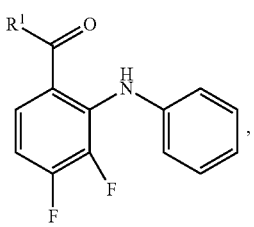

Formula V wherein the R group is defined as above with respect to Formula I.

In particular disclosed embodiments, a disclosed anthranilic amide derivative has the formula illustrated below:

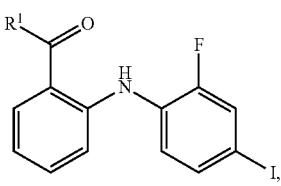

Formula VI wherein the R group is defined as above with respect to Formula I.

In particular disclosed embodiments, a disclosed anthranilic amide derivative has the formula illustrated below:

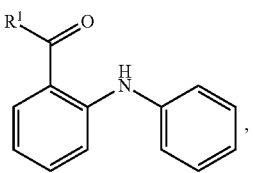

Formula VII wherein the R group is defined as above with respect to Formula I.

In particular disclosed embodiments, a disclosed anthranilic amide derivative has the formula illustrated below:

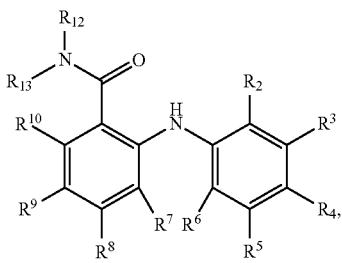

Formula VIII wherein the R group is defined as above with respect to Formula I and $R_{12}$ and $R_{13}$ are independently hydrogen, alkyl, alkenyl, or alkenyl, or taken together with the nitrogen to which they are connected are

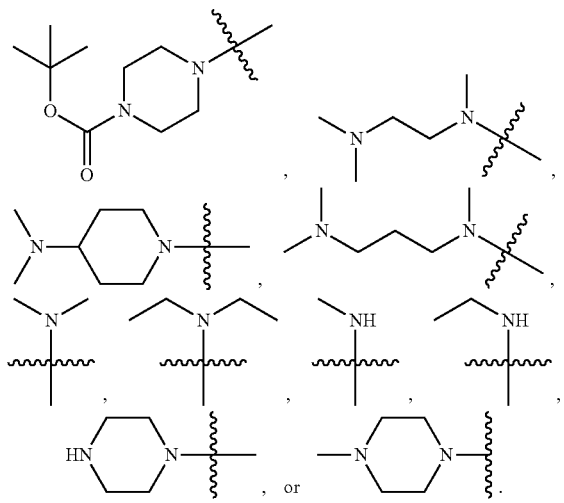

It will be readily apparent to one of ordinary skill in the art that any substituent of any or all of the R groups described above can be selected in any combination or sub-combination.

In specific examples a disclosed anthranilic amide derivative is selected from one of 3,4-difluoro-2-((2-fluoro-4-iodophenyl)amino)benzoic acid (SC-1-180), 3,4-difluoro-2-((2-fluoro-4-iodophenyl)amino)benzamide (SC-1-151 primary amide), N,N-diethyl-3,4-difluoro-2-((2-fluoro-4-iodophenyl)amino)benzamide (SC-1-65), 3,4-difluoro-2-((2-fluoro-4-iodophenyl)amino)-N,N-dimethylbenzamide (SC-1-69), 3,4-difluoro-2-((2-fluoro-4-iodophenyl)amino)-N-methylbenzamide (SC-1-72 amide), Methyl 3,4-difluoro-2-((2-fluoro-4-iodophenyl)amino)benzoate (SC-1-72 ester), Tert-butyl 4-(3,4-difluoro-2-((2-fluoro-4-iodophenyl)amino)benzoyl)piperazine-1-carboxylate (SC-1-75), (3,4-difluoro-2-((2-fluoro-4-iodophenyl)amino)phenyl)(piperazin-1-yl)methanone, hydrochloride (SC-1-79), N-ethyl-3,4-difluoro-2-((2-fluoro-4-iodophenyl)amino)benzamide (SC-1-80), N-(2-(dimethylamino)ethyl)-3,4-difluoro-2-((2-fluoro-4-iodophenyl)amino)-Nmethylbenzamide hydrochloride (SC-1-122), 2-((2-fluoro-4-iodophenyl)amino)benzoic acid (SC-1-14 acid), (2-((2-fluoro-4-iodophenyl)amino)phenyl)(4-methylpiperazin-1-yl)methanone hydrochloride (SC-1-24 amide), 2-(phenylamino)benzoic acid (SC-1-39 acid), (4-methylpiperazin-1-yl)(2-(phenylamino)phenyl)methanone (SC-1-177 amide), 3,4-difluoro-2-(phenylamino)benzoic acid (SC-1-175 acid), 3,4-difluoro-2-(phenylamino)phenyl)(4-methylpiperazin-1-yl)methanone (SC-1-181), 3,4-difluoro-2-((2-fluorophenyl)amino)benzoic acid (SC-2-25 acid), (3,4-difluoro-2-((2-fluorophenyl)amino)phenyl)(4-methylpiperazin-1-yl)methanone mono-fumarate (SC-2-45), 3,4-difluoro-2-((2-fluorophenyl)amino)benzamide (SC-2-37), and 3,4-difluoro-2-((2-fluoro-4-iodophenyl)(methyl)amino)benzoic acid (SC-2-32 acid) or any combination thereof.

"Solvate" means a physical association of a compound with one or more solvent molecules. This physical association involves varying degrees of ionic and covalent bonding, including by way of example covalent adducts and hydrogen bonded solvates. In certain instances the solvate will be capable of isolation, for example when one or more solvent molecules are incorporated in the crystal lattice of the crystalline solid. "Solvate" encompasses both solution-phase and isolable solvates. Representative solvates include ethanol associated compound, methanol associated compounds, and the like. "Hydrate" is a solvate wherein the solvent molecule(s) is/are $H_2O$.

The disclosed compounds also encompass salts including, if several salt-forming groups are present, mixed salts and/or internal salts. The salts are generally pharmaceutically-acceptable salts that are non-toxic. Salts may be of any type (both organic and inorganic), such as fumarates, hydrobromides, hydrochlorides, sulfates and phosphates. In an example, salts include non-metals (e.g., halogens) that form group VII in the periodic table of elements. For example, compounds may be provided as a hydrobromide salt.

Additional examples of salt-forming groups include, but are not limited to, a carboxyl group, a phosphonic acid group or a boronic acid group, that can form salts with suitable bases. These salts can include, for example, nontoxic metal cations which are derived from metals of groups IA, IB, IIA and IIB of the periodic table of the elements. In one embodiment, alkali metal cations such as lithium, sodium or potassium ions, or alkaline earth metal cations such as magnesium or calcium ions can be used. The salt can also be a zinc or an ammonium cation. The salt can also be formed with suitable organic amines, such as unsubstituted or hydroxyl-substituted mono-, di- or tri-alkylamines, in particular mono-, di- or tri-alkylamines, or with quaternary ammonium compounds, for example with N-methyl-N-ethylamine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris (hydroxymethyl)methylamine, N,N-di-lower alkyl-N-(hydroxy-lower alkyl)amines, such as N,N-dimethyl-N-(2-hydroxyethyl)amine or tri-(2-hydroxyethyl)amine, or N-methyl-D-glucamine, or quaternary ammonium compounds such as tetrabutylammonium salts.

Additional counterions for forming pharmaceutically acceptable salts are found in *Remington's Pharmaceutical Sciences*, 22th Edition, Pharmaceutical Publishing, 2012. In one aspect, employing a pharmaceutically acceptable salt may also serve to adjust the osmotic pressure of a composition.

In certain embodiments the compounds used in the method are provided are polymorphous. As such, the compounds can be provided in two or more physical forms, such as different crystal forms, crystalline, liquid crystalline or non-crystalline (amorphous) forms.

C. Use for the Manufacture of a Medicament

Any of the above described compounds (e.g., anthranilic amide derivatives or a hydrate or pharmaceutically acceptable salt thereof) or combinations thereof are intended for use in the manufacture of a medicament for the treatment of cancer. Formulations suitable for such medicaments, subjects who may benefit from same and other related features are described elsewhere herein.

D. Exemplary Methods of Compound Synthesis

The disclosed anthranilic amide derivatives can be synthesized by any method known in the art. Many general references providing commonly known chemical synthetic schemes and conditions useful for synthesizing the disclosed compounds are available (see, e.g., Smith and March, *March's Advanced Organic Chemistry: Reactions, Mechanisms, and Structure*, Fifth Edition, Wiley-Interscience, 2001; or Vogel, *A Textbook of Practical Organic Chemistry, Including Qualitative Organic Analysis*, Fourth Edition, New York: Longman, 1978). Exemplary methods are provided below and in the Examples.

Compounds as described herein may be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via open column chromatography or prep chromatography.

Synthesis of the tetrahalo core: 3,4-difluoro-2-((2-fluoro-4-iodophenyl)amino)benzoic acid (39). Synthesis of the tetrahalo diphenylamine core, 39, was achieved with the lithium amide displacement approach (Scheme 1). This procedure was scaled up to a 4 gram quantity which was necessary for the desired animal experiments with compound 57 (SC-1-151).

Scheme 1: Lithium amide displacement approach.

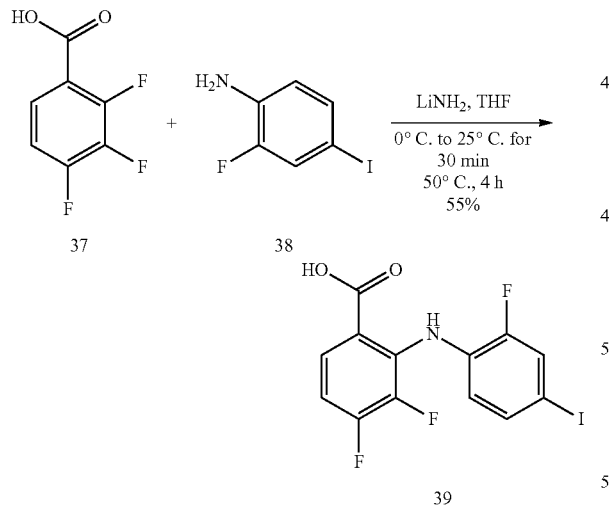

Preferential substitution occurs at the ortho-position as indicated above. Acquisition of the 19F NMR spectra of 2,3,4-trifluorobenzoic acid, 2-fluoro-4-iodoaniline, and 3,4-difluoro-2-((2-fluoro-4-iodophenyl)amino)benzoic acid was conducted using the hetero-nuclear broad-band probe on the 500 MHz instrument.

Synthesis of the tetrahalo amides. The simple amides were envisioned as being readily prepared by the addition of the appropriate amine into the acid chloride that could be prepared from the carboxylic acid 39. This acid, 39, was found to be readily converted into the corresponding acid chloride (Scheme 2). The reagent of choice was oxalyl chloride and catalytic DMF. This system utilized the addition of neat oxalyl chloride to the reaction mixture containing the acid, DMC, and catalytic DMF. The functional role of the DMF is to generate the chloridinium intermediate as shown below. This chloridinium species (84) then activates the carboxylic acid to produce the acid chloride. This reaction proceeded at diffusion-limited rates at 0° C. indicated by the rapid formation and loss of the yellow chloridinium species (Scheme 3). Overall the reaction was completed within 2 hours at or below room temperature to consistently generate acid chloride 79.

Scheme 2: Acid chloride formation.

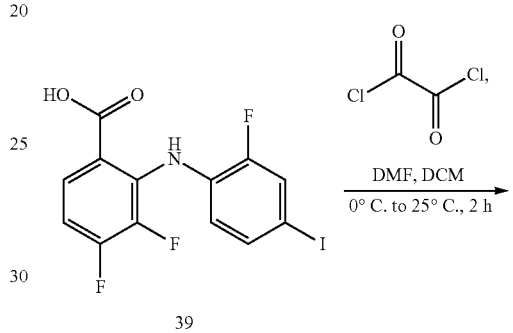

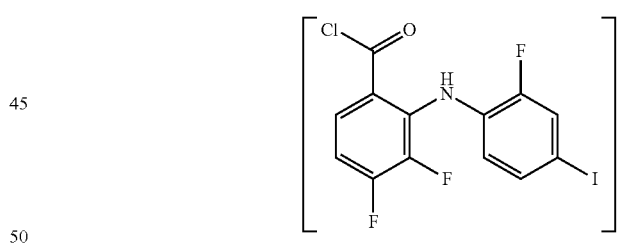

Scheme 3: Synthesis of simple amides using the acid chloride method.

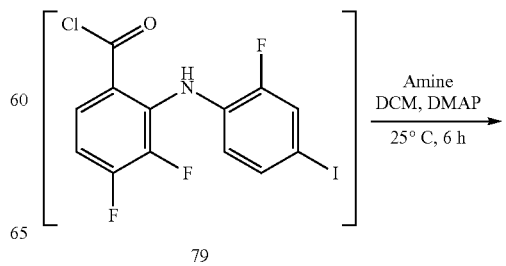

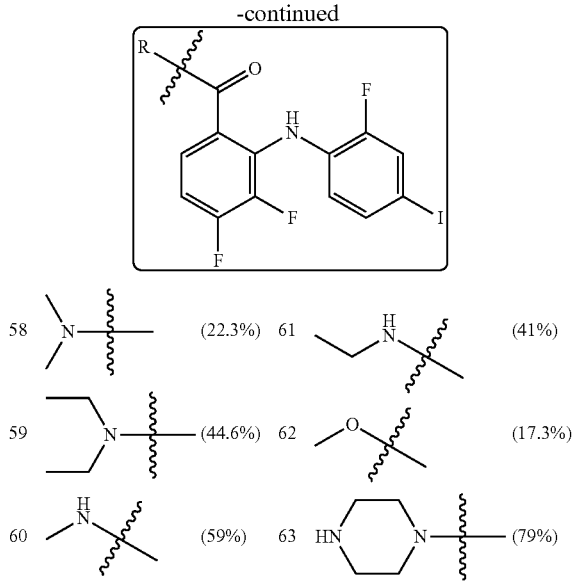

In case of amides bearing a basic amine, this method was not successful. It was decided to use DCC and DIC coupling to form the aide bond more efficiently. In all cases the use of DCC presented a complex mixture which did not permit isolation of clean product. In most cases reactions with DIC proceeded well with a comparatively better cleanup than with DCC.

Synthesis of the trihalo core: 3,4-difluoro-2-((2-fluorophenyl)amino)benzoic acid (68). Synthesis of 3,4-difluoro-2-((2-fluorophenyl)amino)benzoic acid, or the de-iodo variant of diphenylamine acid 68, was prepared using the lithium amide of 2-fluoroaniline in an SNAr displacement on 2,3,4-trifluorobenzoic acid. This conversion proceeded in 59% isolated yield.

Scheme 4: Lithium amide displacement method (see Davis, et al. Org. Process Res. Dev. 2005, 9, 843-846.

An EDCI coupling was used successfully and the fumarate salt of the product 69 was isolated (Scheme 5). The side product urea from EDCI was removed more effectively than the side product from DIC coupling permitting a clean isolation of the basic amine containing product. Formation of the fumarate salt was required because the free base form of the compound was difficult to solidify and recrystallize, as a result direct elemental analysis on the product was unsuccessful. Formation of the HCl salt of 69 produced a very hygroscopic compound that could not be adequately dried to a free-flowing solid. The formation of the fumarate salt addressed isolation and characterization of the desired product in a simple efficient manner.

Scheme 5: Synthesis of 69 Fumarate by EDCI coupling.

Scheme 5: Synthesis of 69 Fumarate by EDCI coupling.

The primary amide derivatives of various terminal ring variations were also synthesized and are described below.

Synthesis of the dihalo core: 3,4-difluoro-2-(phenylamino)benzoic acid (71). The dihalo core, 3,4-difluoro-2-(phenylamino)benzoic acid, retained the central 3,4-difluoro phenyl ring but varied by the lack of halogens on the terminal arene ring. This compound was prepared by the lithium amide displacement method previously described in 43% isolated yield.

Scheme 6: Synthesis of 71 using lithium amide displacement method.

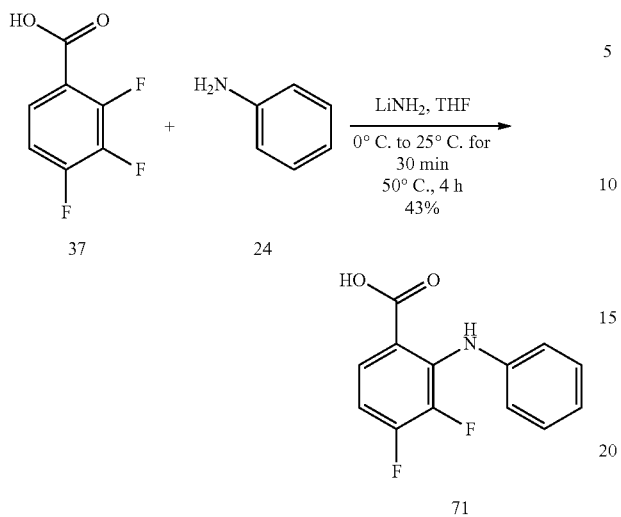

Synthesis of the Dihalo Amides.

Again although the general synthetic strategy proceeding through the acid chloride of carboxylic acid 71 did work, there were complications. The chemical route beginning with the dihaloacid 71 was lower yielding than with the previously described tetrahalo acid 39. A possible explanation is that the attached diphenyl amine was less electron deficient for 71 than for 39. Although the carboxylic acid 71 was anticipated to react in a manner derivativeous to the tetrahalo acid 39 described above, the less electron deficient diphenyl amine may have participated in side reactions including intra- or inter-molecular condensation of the diphenyl amine with the acyl chloride.

Scheme 7: EDCI coupling for the synthesis of 72.

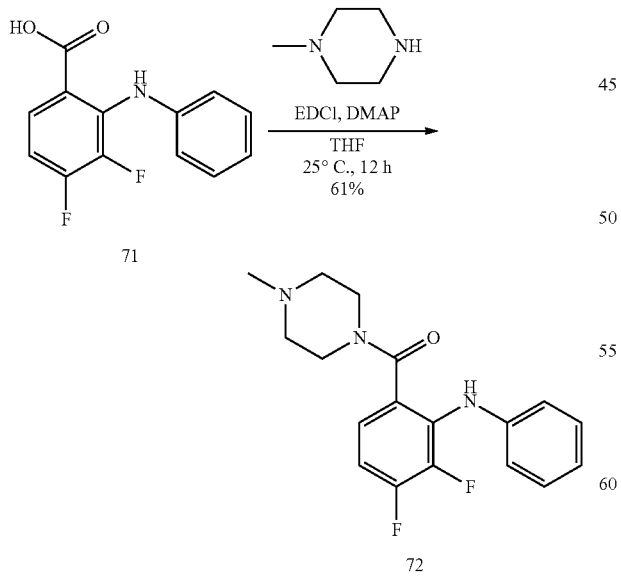

Additionally, the primary amides of these derivatives were also prepared as shown in scheme 8.

Scheme 8: Synthesis of the primary amides 57, 73 and 70.

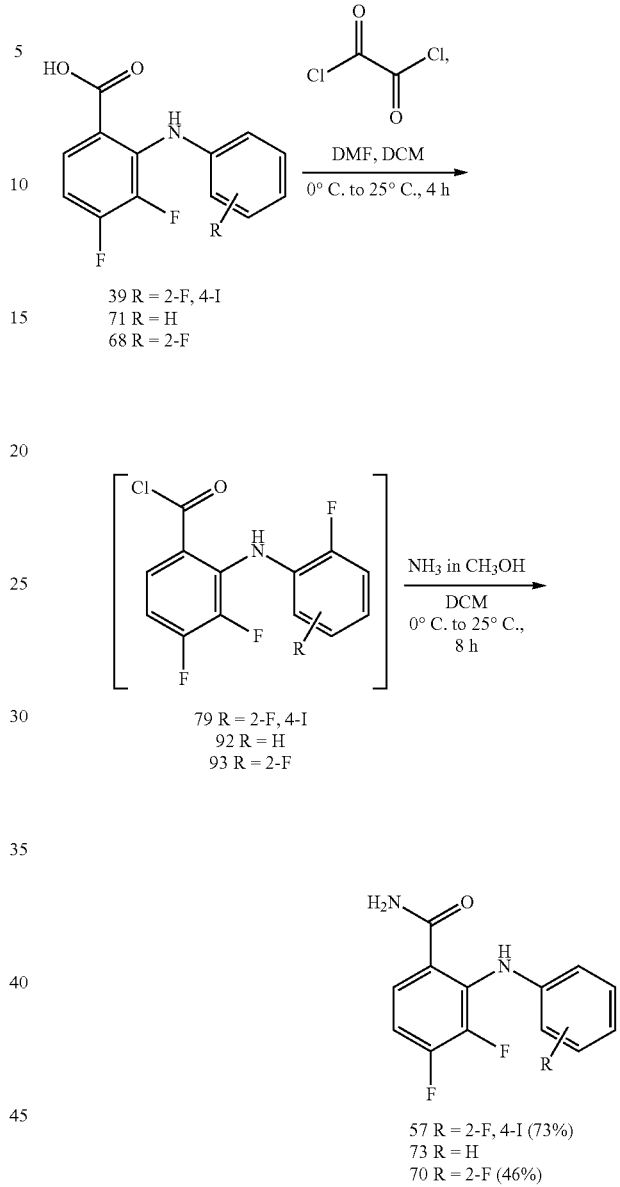

Synthesis of the Unhalogenated Core: 2-(phenylamino) benzoic Acid.

Due to the different substrates required for the desired derivatives, a different synthetic strategy was necessary. A survey of different aryl to nitrogen coupling strategies was conducted (see prior description). Ultimately an Ullmann coupling strategy using the addition of an aniline into the carbon-halogen bond of 2-iodobenzoid acid was selected. This approach used an inexpensive commercially available starting material and used a reasonable electron flow from the electron rich aniline into the electron deficient 2-iodo benzoic acid. An Ullmann coupling strategy worked to give the desired acid in a 44% isolated yield. A survey recent variations recommended the conditions that were ultimately selected and shown in scheme 10. The specific method employed used copper iodide, potassium carbonate, and a mixed solvent system of 9 to 1 DMF to water. Efficient heating was provided by microwave irradiation.

Scheme 9: Ullmann coupling strategy to synthesize 25.

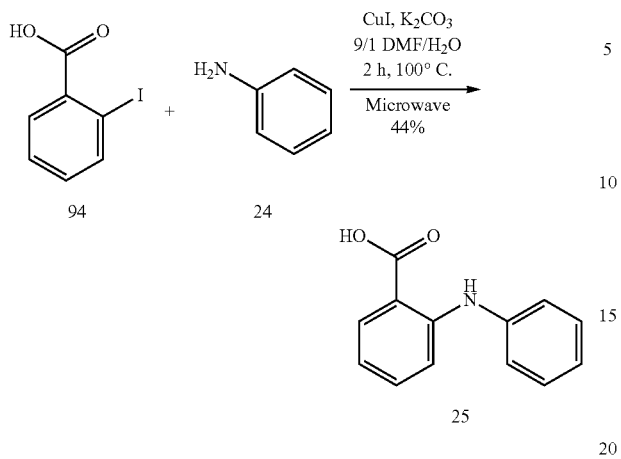

In case of the unhalogenated diphenylamine, compound 25, a different amide-forming strategy was required. The acid chloride method described previously did not work. Probable reasons for the failure of this strategy include the increased nucleophilicity of the amine of compound 25 resulting from the absence of electron-withdrawing groups compared to compounds previously synthesized in the series described above. This greater electron density in compound 95 may have led to self-condensations in either inter- or an intra-molecular manner. This explanation is consistent with the observed consumption of starting material with no isolable product.

The next approach attempted for the synthesis of compound 75 was synthesis of the Boc-piperazine derivative 96 followed conversion to the piperazine derivative. Synthesis to the tertiary amine using an Eschweiler-Clarke reaction was planned. However, the Eschweiler-Clarke product could not be isolated (Scheme 10). Learning from prior reactions, this strategy was abandoned for the far more efficient route (DIC coupling) presented in Scheme 11. This DIC coupling was successful and the product was isolated in a modest yet welcome 17% yield.

Scheme 11: DIC coupling method to synthesize 75.

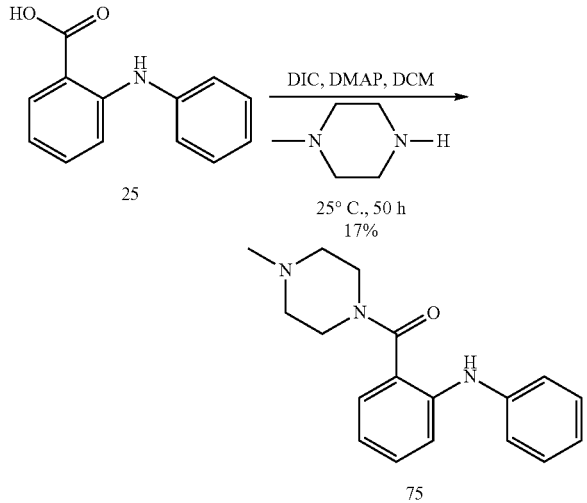

Scheme 12: Synthesis of amides 75 and 74.

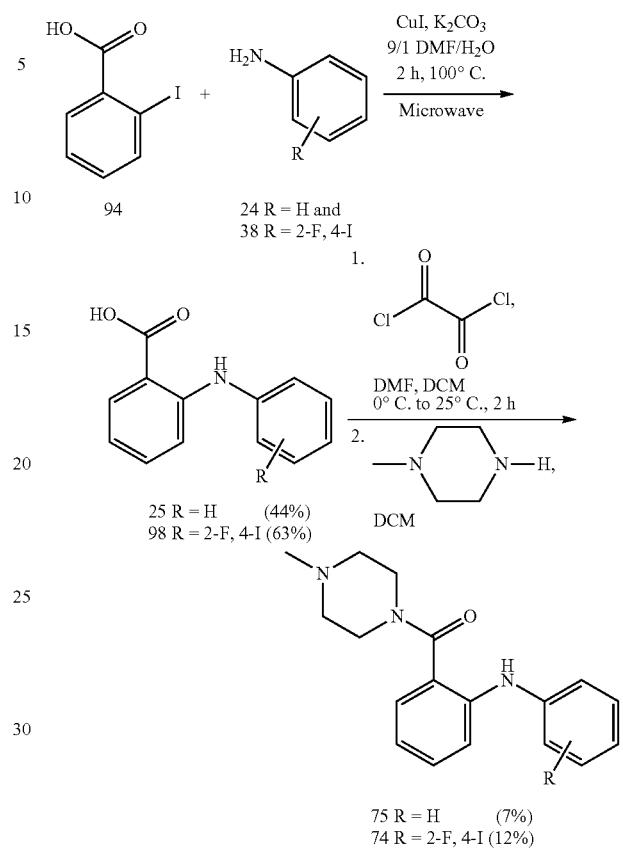

An attempted SNAr nucleophilic of the lithium amid of 2-fluoro-4-iodoanaline into 2-iodobenzoic acid with excess lithium amide in THF using the now standard procedure of Davis was unsuccessful. This was probably due to a more electropositive carbon at the 2 position when compared to the prior substrate, 2,3,4-trifluorobenzoic acid. Again, based on prior observations, alteration of the synthetic strategy to use an Ullmann coupling was shown to be successful and proceeded reliably in 40-60% isolated then recrystallized yield.

Synthesis of the N-Methyl Diphenylamine Core:

An Eschweiler-Clarke reaction was examined as an initial strategy in an attempt to prepare 3,4-difluoro-2-((2-fluoro-4-iodophenyl)(methyl)amino)benzoic acid, compound 76. The use of standard microwave reaction conditions were examined, but the desired product could not be isolated. Another strategy was attempted using sodium hydride abstraction of the proton from the diphenyl amine nitrogen atom followed by alkylation with methyl iodide. A crude TLC analysis revealed many spots, attempted separation by column chromatography was unsuccessful.

After the two unsuccessful synthetic approaches a very different strategy was pursued. Alkylation was conducted on the simple aniline precursor, 2-fluoro-4-iodoaniline, to successfully prepare the mono N-methylated product, 2-fluoro-4-iodo-N-methylaniline, shown in scheme 34.114 This secondary aniline was then coupled to 2,3,4-trifluorobenzoic acid using the standard SNAr lithium amide displacement approach.

Scheme 13: Monomethylation reaction of 38.

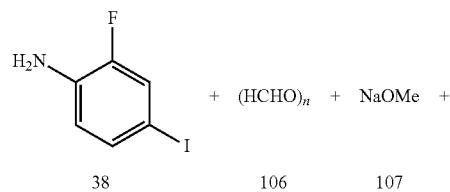

Scheme 14: Synthesis of acid 76 by lithium amide displacement method.

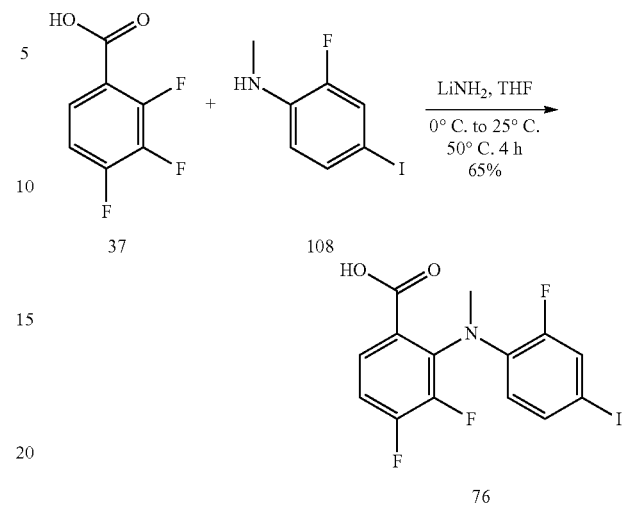

Additional synthesis schemes can be found in FIGS. 4-8.

TABLE 1

Structure, Identification and Activity of Novel Compounds.

| Structure | Compound Reference | Synonym | cellular pERK1/2 decrease (%) | cellular pERK5 decrease (%) |
|---|---|---|---|---|
| (C$_{18}$H$_{19}$F$_2$N$_3$O) | Compound 15 | SC-1-181, Compound 72 | activation (+8.5) | 82.4 |
| (C$_{17}$H$_{16}$F$_3$IN$_2$O) | Compound 9b | B9, SC-1-65, Compound 59 | 5.5 | activation (−7.4) |

TABLE 1-continued

Structure, Identification and Activity of Novel Compounds.

| Structure | Compound Reference | Synonym | cellular pERK1/2 decrease (%) | cellular pERK5 decrease (%) |
|---|---|---|---|---|
| C₁₅H₁₂F₃IN₂O | Compound 9a | C9, SC-1-69, Compound 58 | 87.3 | 0.2 |
| C₁₄H₁₀F₃IN₂O | Compound 9c | D9, SC-1-72 amide, Compound 60 | 99.6 | 20.4 |
| C₂₂H₂₃F₃IN₃O₃ | Compound 9g | F9, SC-1-75 | 70.9 | 8.4 |
| C₁₃H₇F₃INO₂ | Compound 7 | SC-1-180, SC-1-148, Compound 39 | 98.5 | 20.1 |

TABLE 1-continued

Structure, Identification and Activity of Novel Compounds.

| Structure | Compound Reference | Synonym | cellular pERK1/2 decrease (%) | cellular pERK5 decrease (%) |
|---|---|---|---|---|
| $C_{14}H_9F_3INO_2$ | Compound 9e SC-1-72 Ester | E9, Compound 62 | 98.93 | 13 |
| $C_{17}H_{18}ClFIN_3O$ | Compound 24 | A9, SC-1-24, Compound 74 | 33.5 | 20.9 |
| $C_{17}H_{15}F_3IN_3O$ | Compound 9f | G9, SC-1-79, Compound 63 | 98.99 | activation (+4.4) |
| $C_{15}H_{12}F_3IN_2O$ | Compound 9d | H9, SC-1-80, Compound 61 | 98.63 | 8.5 |

TABLE 1-continued

Structure, Identification and Activity of Novel Compounds.

| Structure | Compound Reference | Synonym | cellular pERK1/2 decrease (%) | cellular pERK5 decrease (%) |
|---|---|---|---|---|
| $C_{18}H_{19}F_3IN_3O$ | Compound 9h | D10, SC-1-122 | 28.2 | 9 |
| $C_{14}H_{12}ClNO_2$ | SQ-1-145 | tolfenamic acid, A12 | | |
| $C_{18}H_{21}N_3O$ | Compound 23 | A13, SC-1-177, Compound 75 | 29.6, activation (+5.5) | 40.4, 4.8 |
| $C_{13}H_8F_3IN_2O$ | Compound 3 | IC-D-122a/ IC-3-99, SC-1-151/ SC-1-172/ SC-2-30, Compound 57 | 99.2, 90.9 | 56.5, 48.4 |
| $C_{18}H_{17}F_3IN_3O$ | IC-D-122b | | 39 | 33 |

TABLE 1-continued

Structure, Identification and Activity of Novel Compounds.

| Structure | Compound Reference | Synonym | cellular pERK1/2 decrease (%) | cellular pERK5 decrease (%) |
|---|---|---|---|---|
| $C_{17}H_{14}F_3IN_2O_2$ | IC-3-93 | IC-D-122c | 47.8 | 76.3 |
| $C_{18}H_{16}F_3IN_2O$ | IC-3-97 | IC-D-122d | 42.4 | 87.1 |
| $C_{15}H_{12}F_3IN_2O_2$ | IC-3-102 | IC-D-122e | −31.1 | 47.9 |
| $C_{16}H_{12}F_3IN_2O_4$ | IC-3-111 | IC-D-122f | 85 | 205.8 |

TABLE 1-continued

Structure, Identification and Activity of Novel Compounds.

| Structure | Compound Reference | Synonym | cellular pERK1/2 decrease (%) | cellular pERK5 decrease (%) |
|---|---|---|---|---|
| $C_{16}H_{12}F_3IN_2O_4$ | IC-3-117 | IC-D-122g | 80.8 | 126.9 |
| $C_{14}H_{13}ClN_2O$ | SQ-1-182 | | | |
| $C_{13}H_9F_2NO_2$ | Compound 12 | SC-1-175, Compound 71 | | |
| $C_{13}H_8F_3NO_2$ | Compound 13 | SC-2-25, Compound 68 | | |
| $C_{14}H_9F_3INO_2$ | SC-2-32 | Compound 76 | | |

E. Methods of Treatment

Methods are disclosed herein for treating a subject with cancer, suspected of having cancer or at high risk of developing cancer with or more of the disclosed anthranilic amide derivatives. The methods can include selecting an individual that is in need or treatment, such as a subject having cancer, for example diagnosed with a solid tumor, for example a breast cancer tumor, a prostate cancer tumor and/or a pancreatic tumor. Typical subjects intended for treatment with a disclosed anthranilic amide derivative include humans, as well as non-human primates and other animals, such as mice. After selection, the subject is administered a therapeutically effective amount of a disclosed anthranilic amide derivative, thereby treating cancer. In some examples, the disclosed anthranilic amide derivative is provided as a pharmaceutical composition or compositions. Also disclosed are methods for inhibiting MEK1/2 and/or MEK5 in a subject, for example be administering to a subject an effective amend of a disclosed anthranilic amide derivative. Further disclosed are methods of inhibiting and/or reversing the epithelial-mesenchymal transition, for example in a cancer cell.

The administration of the disclosed anthranilic amide derivative can be for either prophylactic or therapeutic purpose. When provided prophylactically, the disclosed anthranilic amide derivative is provided in advance of any symptom. The prophylactic administration of the compounds serves to prevent or ameliorate any subsequent disease process. When provided therapeutically, the compounds are provided at (or shortly after) the onset of a symptom of disease or at any time during the course of the disease.

For prophylactic and therapeutic purposes, the disclosed anthranilic amide derivative can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition.

Determination of effective dosages is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the disclosed anthranilic amide derivative (for example, amounts that are effective to alleviate one or more symptoms of a targeted disease or condition). In alternative embodiments, an effective amount or effective dose of the disclosed anthranilic amide derivative may simply inhibit or enhance one or more selected biological activities correlated with a disease or condition.

The actual dosage of the disclosed anthranilic amide derivative will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the disclosed anthranilic amide derivative for eliciting the desired activity or biological response in the subject. Dosage regimens can be adjusted to provide an optimum prophylactic or therapeutic response.

A therapeutically effective amount is also one in which any toxic or detrimental side effects of the compound and/or other biologically active agent is outweighed in clinical terms by therapeutically beneficial effects. A non-limiting range for a therapeutically effective amount of a disclosed anthranilic amide derivative within the methods and formulations of the disclosure is about 0.0001 µg/kg body weight to about 10 mg/kg body weight per dose, such as about 0.0001 µg/kg body weight to about 0.001 µg/kg body weight per dose, about 0.001 µg/kg body weight to about 0.01 µg/kg body weight per dose, about 0.01 µg/kg body weight to about 0.1 µg/kg body weight per dose, about 0.1 µg/kg body weight to about 10 µg/kg body weight per dose, about 1 µg/kg body weight to about 100 µg/kg body weight per dose, about 100 µg/kg body weight to about 500 µg/kg body weight per dose, about 500 µg/kg body weight per dose to about 1000 µg/kg body weight per dose, or about 1.0 mg/kg body weight to about 10 mg/kg body weight per dose.

Dosage can be varied by the attending clinician to maintain a desired concentration at a target site. Higher or lower concentrations can be selected based on the mode of delivery, for example, trans-epidermal, rectal, oral, pulmonary, intranasal delivery, intravenous or subcutaneous delivery. To achieve the same serum concentration level, for example, slow-release particles with a release rate of 5 nanomolar (under standard conditions) would be administered at about twice the dosage of particles with a release rate of 10 nanomolar.

When a disclosed anthranilic amide derivative is administered to a subject, the administration can be concurrent or sequential. Sequential administration can be separated by any amount of time, so long as the desired affect is achieved. Multiple administrations of the compositions described herein are also contemplated.

The specific dose level and frequency of dosage for any particular subject may be varied and will depend upon a variety of factors, including the activity of the specific compound, the extent of existing disease activity, the age, body weight, general health, sex, diet, mode and time of administration, rate of excretion, drug combination, and severity of the condition of the host undergoing therapy.

F. Pharmaceutical Compositions

Compositions, such as therapeutic or pharmaceutical compositions, are provided that include one or more disclosed anthranilic amide derivatives. It is desirable to prepare the inhibitor of MEK1/2 and/or MEK 5 activity as a pharmaceutical composition appropriate for the intended application, for example to inhibit or treat a cellular proliferative or a cellular movement or cellular dissemination disorder. Accordingly, methods for making a medicament or pharmaceutical composition containing a disclosed anthranilic amide derivative are included herein. The disclosed anthranilic amide derivatives can be prepared for administration alone or with other active ingredients, such as other chemotherapeutics.

Pharmaceutical compositions including a disclosed anthranilic amide derivative can be administered to subjects by a variety of routes. These include oral, nasal (such as intranasal), ocular, buccal, enteral, intravitral, or other mucosal (such as rectal or vaginal) or topical administration. Alternatively, administration will be by orthotopic, intradermal subcutaneous, intramuscular, parentral intraperitoneal, or intravenous injection routes. Such pharmaceutical compositions are usually administered as pharmaceutically acceptable compositions that include physiologically acceptable carriers, buffers or other excipients.

Typically, preparation of a pharmaceutical composition (for example, for use as a medicament or in the manufacture of a medicament) entails preparing a pharmaceutical composition that is essentially free of pyrogens, as well as any other impurities that could be harmful to humans or animals. The disclosed anthranilic amide derivative may be included in pharmaceutical compositions (including therapeutic and prophylactic formulations), which are typically combined together with one or more pharmaceutically acceptable vehicles or carriers and, optionally, other therapeutic ingredients.

To formulate the pharmaceutical compositions, the disclosed anthranilic amide derivative can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The disclosed anthranilic amide derivative can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly (hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, and microspheres.

The disclosed anthranilic amide derivative can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., J. Pharmacy Pharmacol. 43:1-5, 1991), and dispersed in a biocompatible dispersing medium, which yields sustained delivery and biological activity over a protracted time.

The disclosed anthranilic amide derivative can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the disclosed anthranilic amide derivative can be also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

For prophylactic and therapeutic purposes, the pharmaceutical compositions can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein.

Therapeutic compositions that include a disclosed anthranilic amide derivative can be delivered by way of a pump (see Langer, supra; Sefton, CRC Crit. Ref. Biomed. Eng. 14:201, 1987; Buchwald et al., Surgery 88:507, 1980; Saudek et al., N. Engl. J. Med. 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (Science 249:1527-33, 1990).

In one example, a pump is implanted (for example see U.S. Pat. Nos. 6,436,091; 5,939,380; and 5,993,414). Implantable drug infusion devices are used to provide patients with a constant and long-term dosage or infusion of a therapeutic agent. Such device can be categorized as either active or passive.

Active drug or programmable infusion devices feature a pump or a metering system to deliver the agent into the patient's system. An example of such an active infusion device currently available is the Medtronic SYNCHROMED™ programmable pump. Passive infusion devices, in contrast, do not feature a pump, but rather rely upon a pressurized drug reservoir to deliver the agent of interest. An example of such a device includes the Medtronic ISOMED™.

In particular examples, therapeutic compositions are administered by sustained-release systems. Suitable examples of sustained-release systems include suitable polymeric materials (such as, semi-permeable polymer matrices in the form of shaped articles, for example films, or mirocapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracistemally, intraperitoneally, topically (as by powders, ointments, gels, drops or transdermal patch), or as an oral or nasal spray. Sustained-release matrices include polylactides (U.S. Pat. No. 3,773, 919, EP 58,481), copolymers of L-glutamic acid and gamma-ethyl-L-glutamate (Sidman et al., Biopolymers 22:547-556, 1983, poly(2-hydroxyethyl methacrylate)); (Langer et al., J. Biomed. Mater. Res. 15:167-277, 1981; Langer, Chem. Tech. 12:98-105, 1982, ethylene vinyl acetate (Langer et al., Id.) or poly-D-(−)-3-hydroxybutyric acid (EP 133,988).

Polymers can be used for ion-controlled release. Various degradable and nondegradable polymeric matrices for use in controlled drug delivery are known in the art (Langer, Accounts Chem. Res. 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., Pharm. Res. 9:425, 1992; and Pec, J. Parent. Sci. Tech. 44(2):58, 1990). Alternatively, hydroxyapatite has been used as a microcarrier for controlled release of proteins (Ijntema et al., Int. J. Pharm. 112:215, 1994). In yet another aspect, liposomes are used for controlled release as well as drug targeting of the lipid-capsulated drug (Betageri et al., Liposome Drug Delivery Systems, Technomic Publishing Co., Inc., Lancaster, Pa., 1993). Numerous additional systems for controlled delivery of therapeutic proteins are known (for example, U.S. Pat. Nos. 5,055,303; 5,188,837; 4,235,871; 4,501,728; 4,837, 028; 4,957,735; and 5,019,369; 5,055,303; 5,514,670; 5,413,797; 5,268,164; 5,004,697; 4,902,505; 5,506,206; 5,271,961; 5,254,342; and 5,534,496).

The subject matter of the present disclosure is further illustrated by the following non-limiting Examples.

EXAMPLES

Example 1

Experimental

Figure 2:
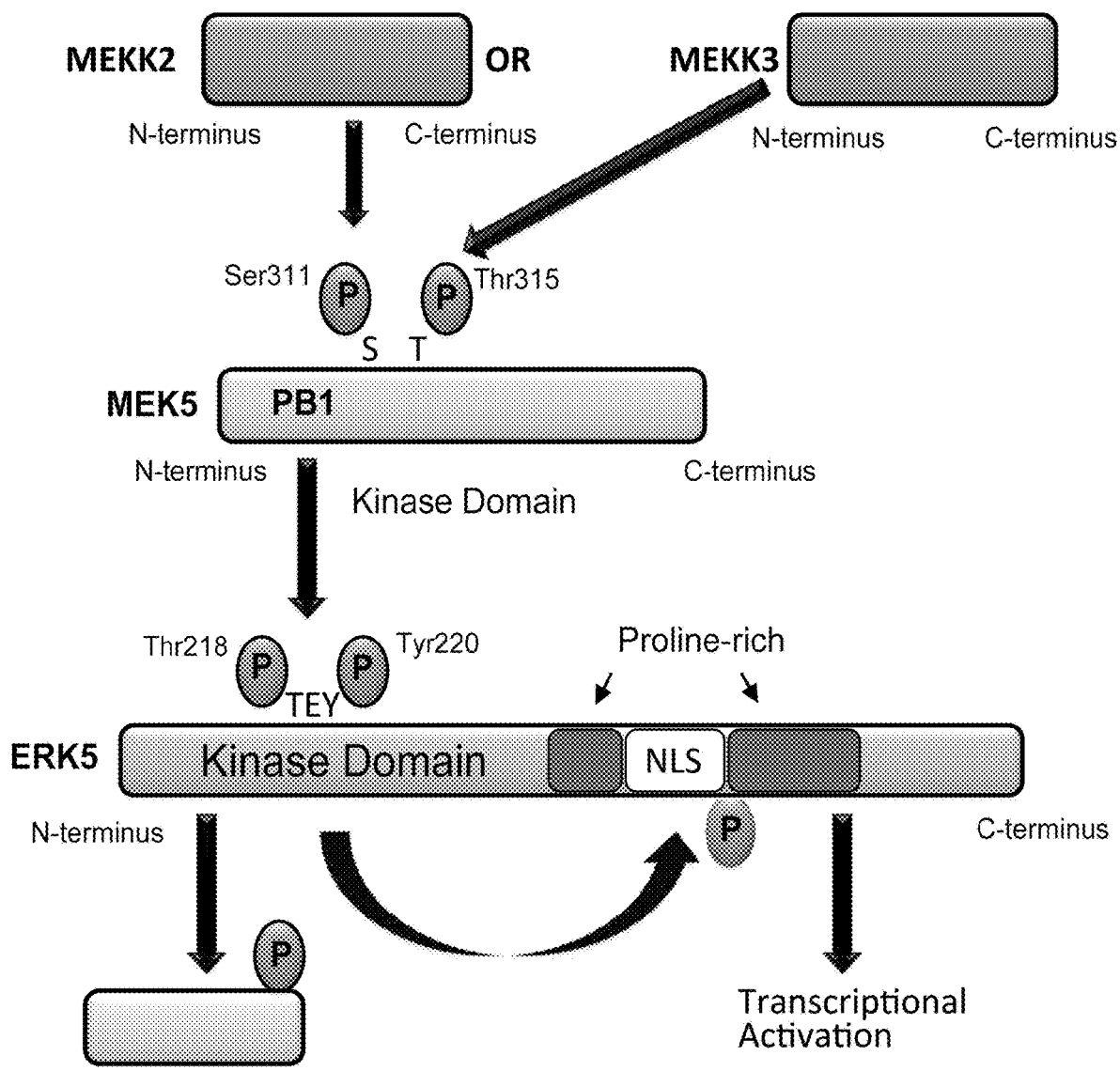
FIG. 2 is a diagram of the MEK5 signaling pathway.
Figure 3:
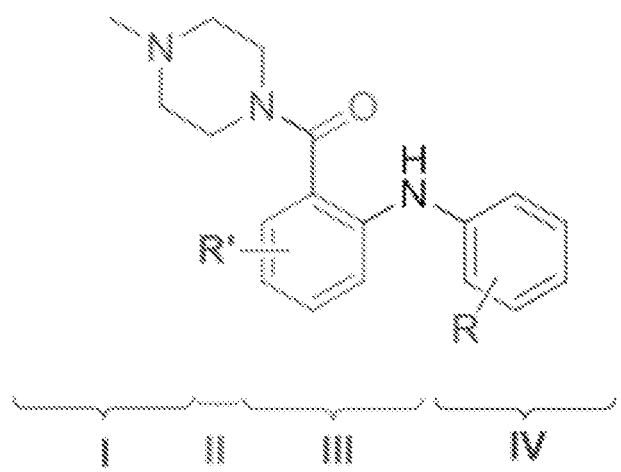
FIG. 3 is a diagram showing the rationale design of the disclosed compounds.
Figure 4:
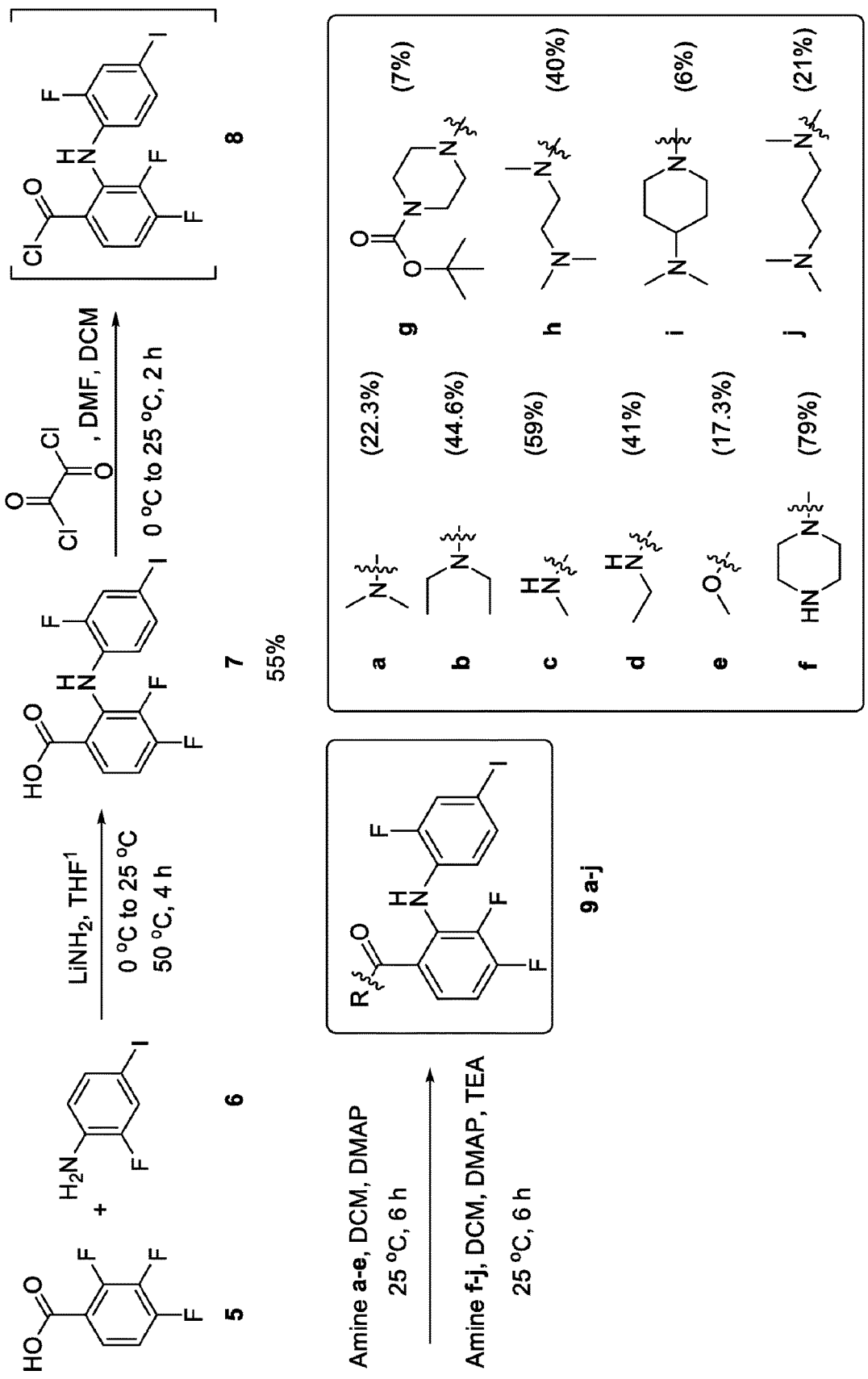
FIG. 4 is an exemplary synthetic scheme for compounds 9a-j via acid chloride.

FIG. 1 and FIG. 2 show the MAPK signaling pathways and the MEK5 signaling pathway, respectively. In order to develop a strategy to design compounds to inhibit MEK5, a cellular assay of the inhibition of EGF-mediated formation of pERK isoforms by previously synthesized inhibitors in HEK 293 (kidney) and BT-474 cell lines was performed. The design strategy focused on four areas, as shown in FIG. 3. Side chain variations were targeted to modify solubility and were used to examine MEK5 predicted interactions. Design strategy areas two and three concentrated on amide ariations and the central arene, respectively. The fourth area is the terminal arene, where the goal was to achieve the minimal necessary substitution and to drive MEK5 selective interactions.

Figure 5:
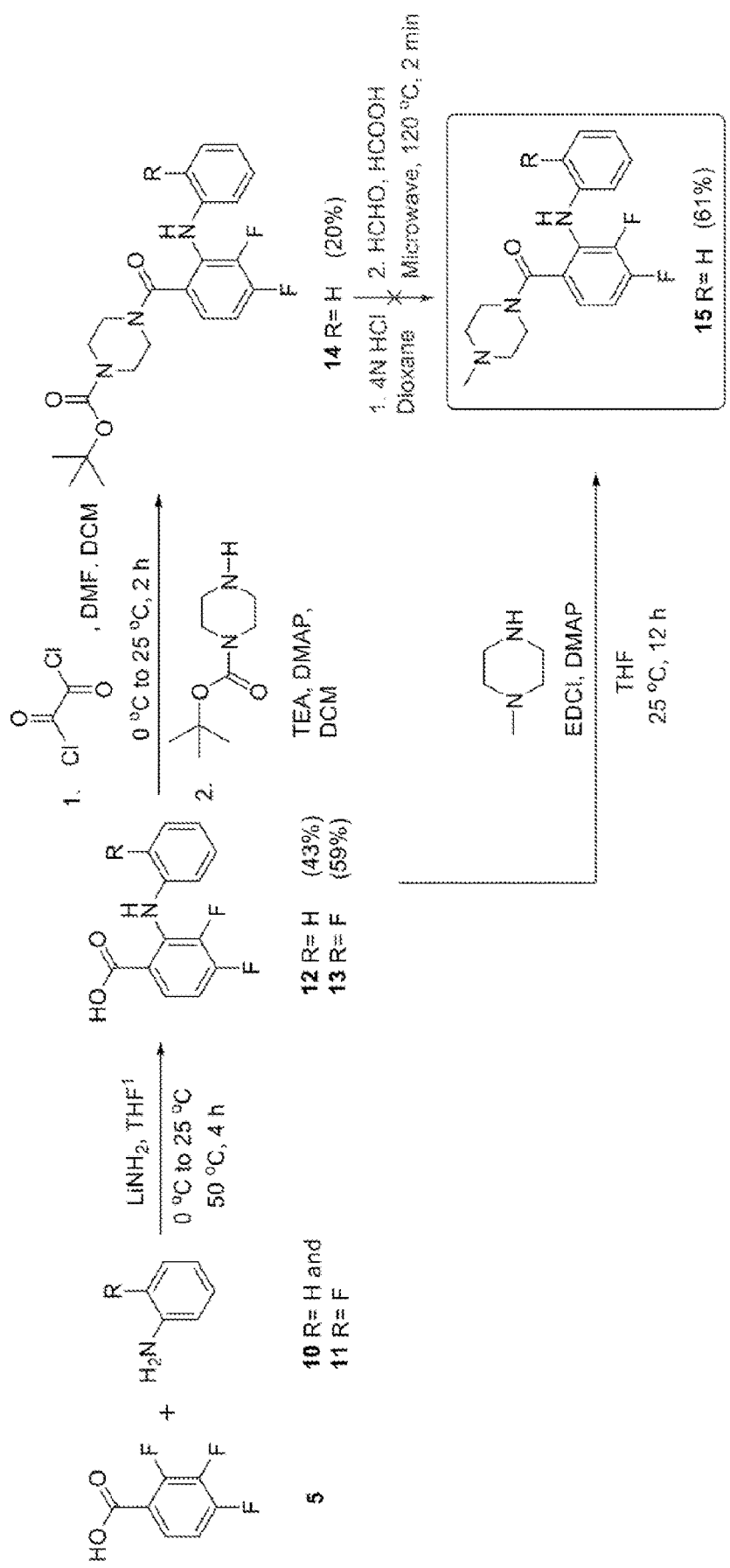
FIG. 5 is an exemplary synthetic scheme for compound 15 by EDCI coupling.
Figure 6:
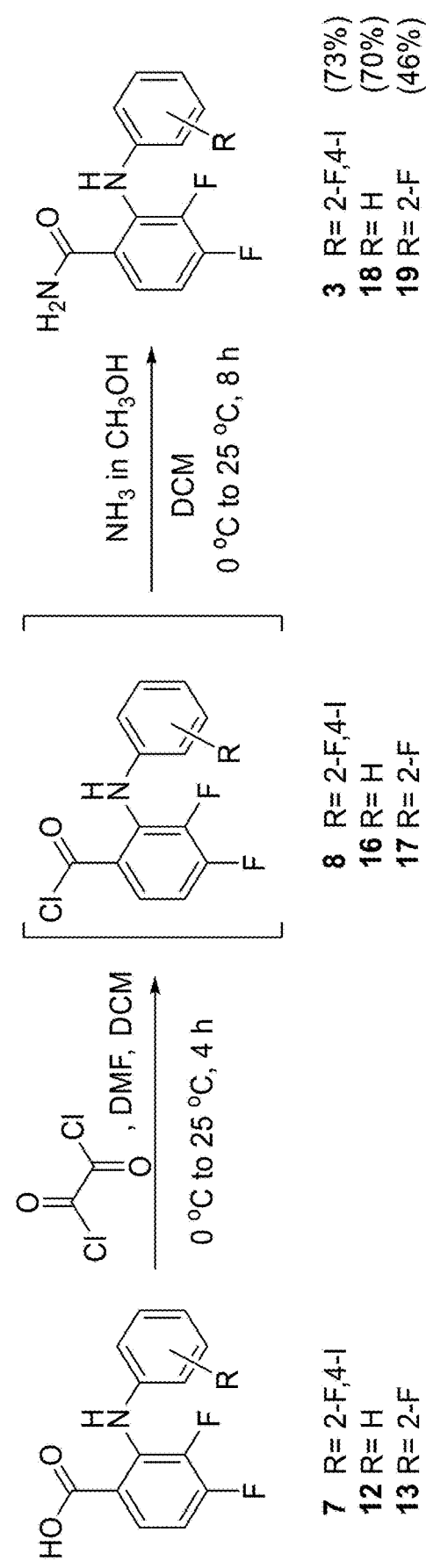
FIG. 6 is an exemplary synthetic scheme for primary amides 3, 18 and 19.
Figure 7:
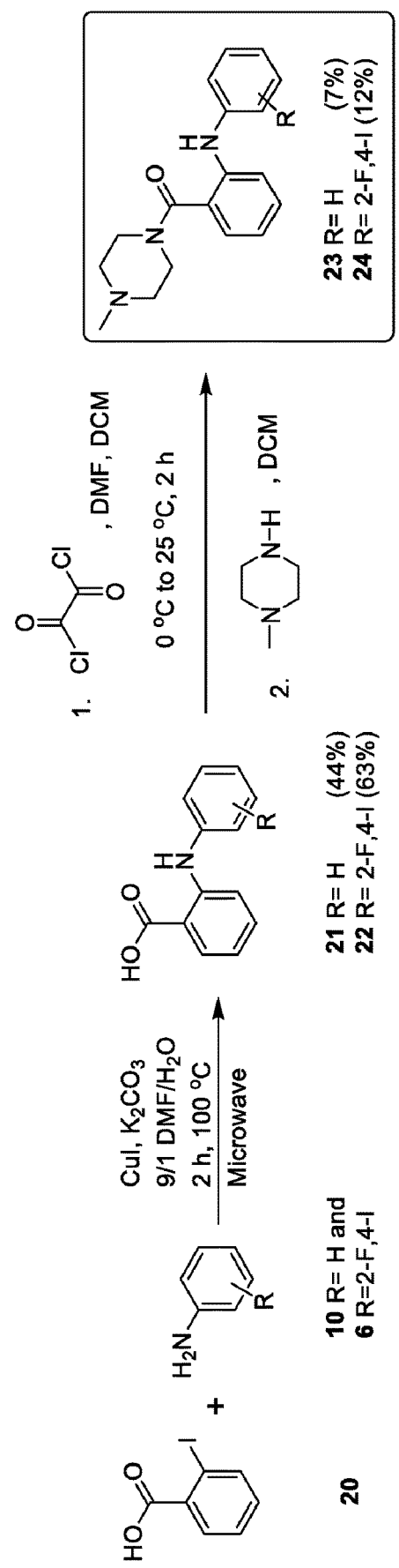
FIG. 7 is an exemplary synthetic scheme for compounds 23, 24 via acid chloride.

Compounds were synthesized using a number of schemes under two broad approaches. The first approach was lithium amide displacement. Compounds 9a-9j were synthesized using the scheme shown in FIG. 4. Compound 15 was synthesized by EDCI coupling, as shown in FIG. 5. FIG. 6 shows the synthesis of primary amides compounds 3, 18 and 19.

Figure 8:
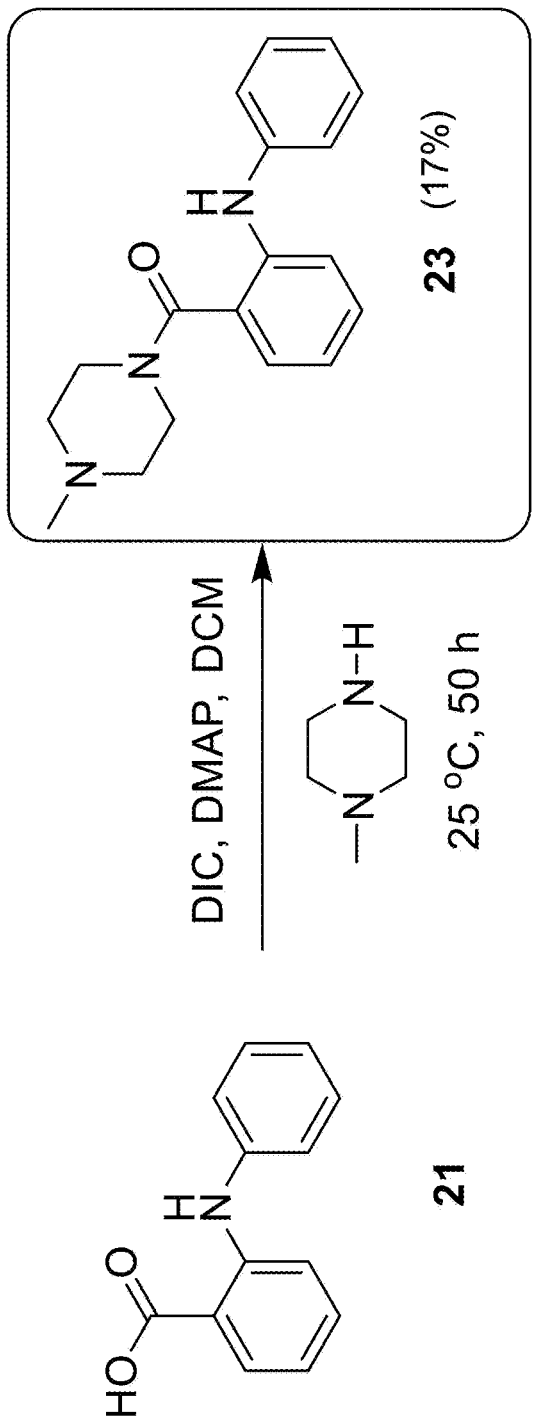
FIG. 8 is an exemplary synthetic scheme for compound 23 by DIC coupling.

The second approach used Ullmann Coupling. Compound 23 and compound 24 were synthesized via acid chloride, using the scheme shown in FIG. 7. The synthesis of compound 23 was improved by using DIC coupling, as shown in FIG. 8.

A number of compounds were tested for their potential as MEK5 inhibitors. The MDA-MB-231 triple negative breast cancer cell line was pretreated with 10 µM of compounds 24, 9b, 9a, 9c, 9e, 9f, 9d, 9h, 23, 7, and 15 for 30 minutes followed by stimulation with epidermal growth factor (EGF, 50 ng/mL) for 15 minutes. Vehicle-treated cells and known MEK1/2 inhibitor cells were pretreated with DMSO and U0126 respectively for 30 minutes prior to EGF stimulation for 15 minutes. Protein visualization and quantification analysis was performed using LI-COR Odyssey Imager. The results of the Western blot analysis are shown in FIG. 9. * $P<0.05$ vs. Vehicle, one-way ANOVA followed by Tukey-Kramer test (n=3). A table of the results of a cellular assay of inhibition of EGF-mediated formation of pERK isoforms is shown in FIG. 10.

Figure 11:
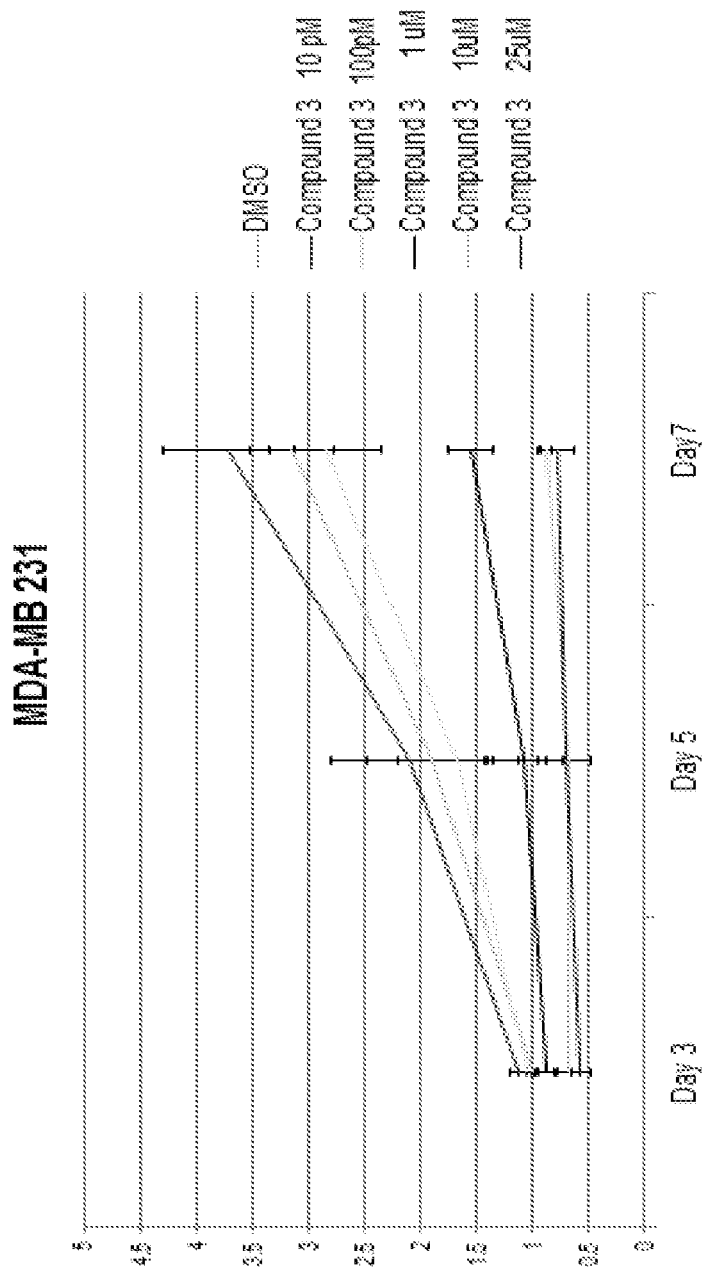
FIG. 11 is a graph showing the results of MDA-MB 231 proliferation studies. MDA-MB 231 cells were used as they express the triple negative cancer phenotype. Compound 3 was selected due to potency in inhibition of both MEK1/2 and MEK5. MDA-MB 231 cells were plated at 10,000 cells per well in a 96 well TC plate in 5% Charcoal-Dextran stripped media and incubated overnight at 37° C. in 5% $CO_2$. The cells were treated with drug or vehicle the following day. Plates were harvested on days 3, 5 and 7 and stained with Crystal Violet. Cells were observed for morphological changes under an inverted microscope. The cells were washed, lysed, and the absorbance of Crystal Violet sequestered in living cells was determined at 630 nM. Wells were conducted in duplicate. Experiments were run in triplicate. Cells were normalized to initial cell count.
Figure 13:
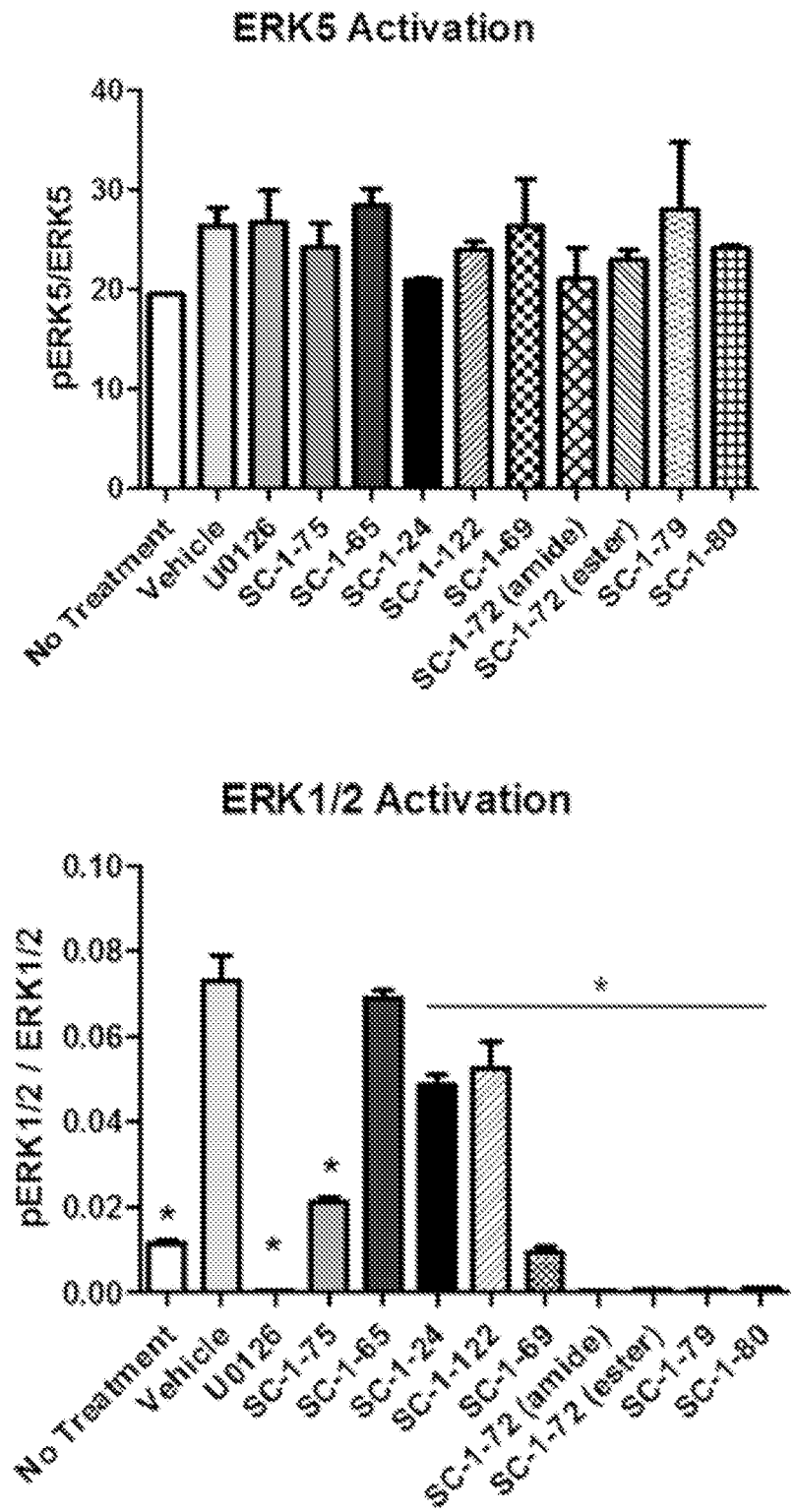
FIG. 13 is a set of bar graphs illustrating the results of the tests in Example 3.
Figure 15:
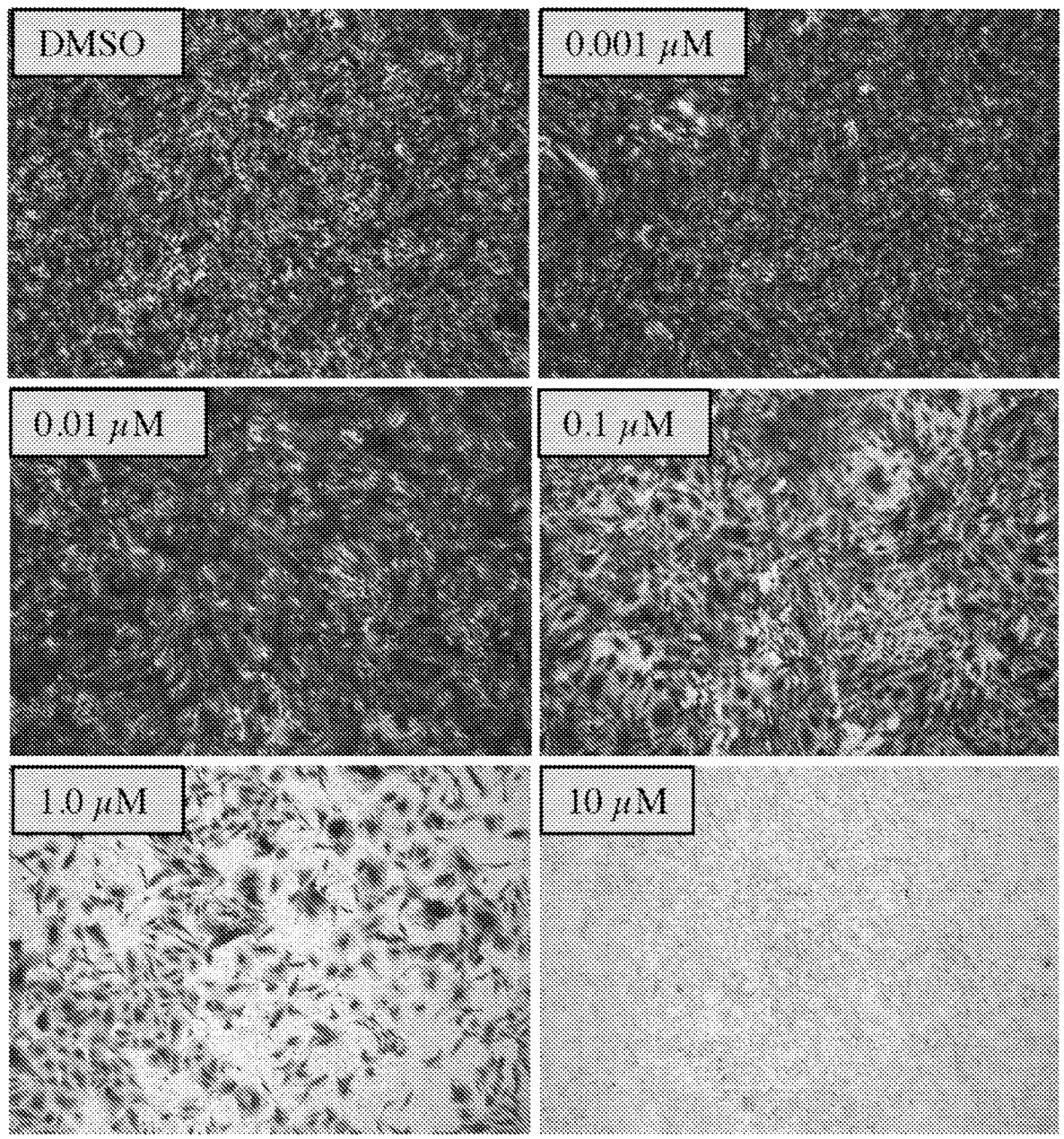
FIG. 15 is a set of digital images illustrating the results of the tests in Example 3.
Figure 16:
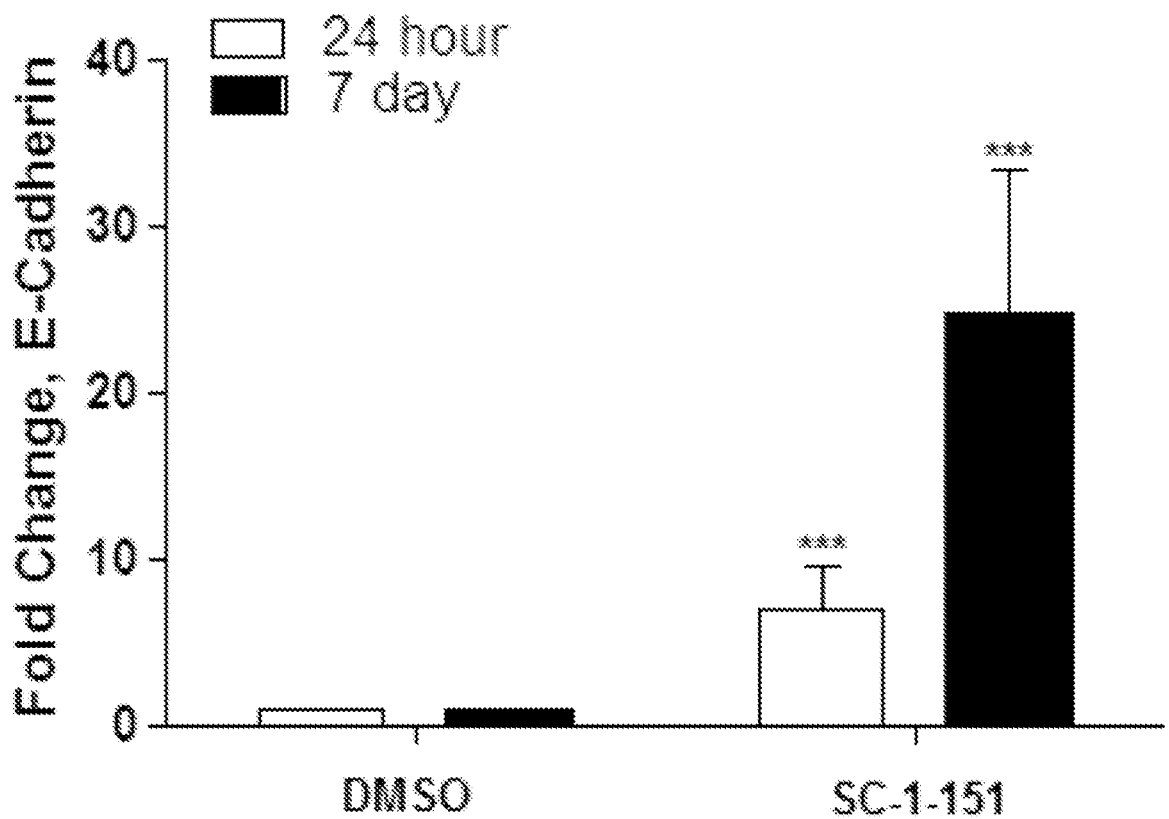
FIG. 16 is a bar graph illustrating the results of the tests in Example 3.
Figure 17:
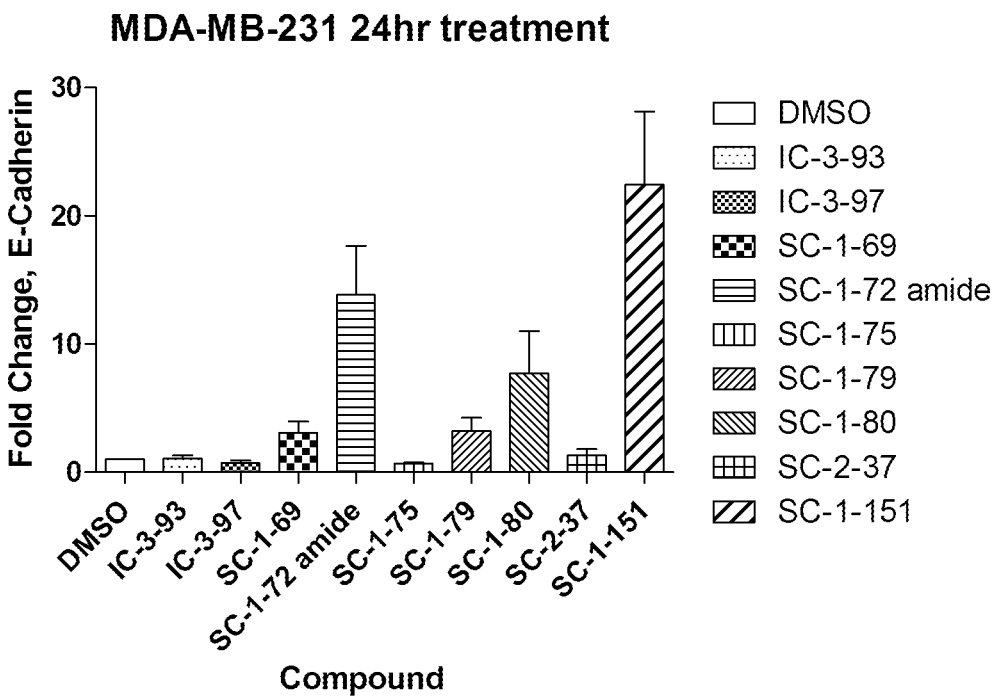
FIG. 17 is a bar graph showing E-cadherin expression of MDA-MB-231 breast cancer cells after 1 μM treatment. The compounds alter expression of EMT genes in metastatic breast cancer cells. MDA-MB-231 were grown in 5% charcoal-stripped phenol red free DMEM for 48 hours and treated with compounds (1 μM). After 24 hours, cells were collected for qPCR analysis of E-cadherin.
Figure 18:
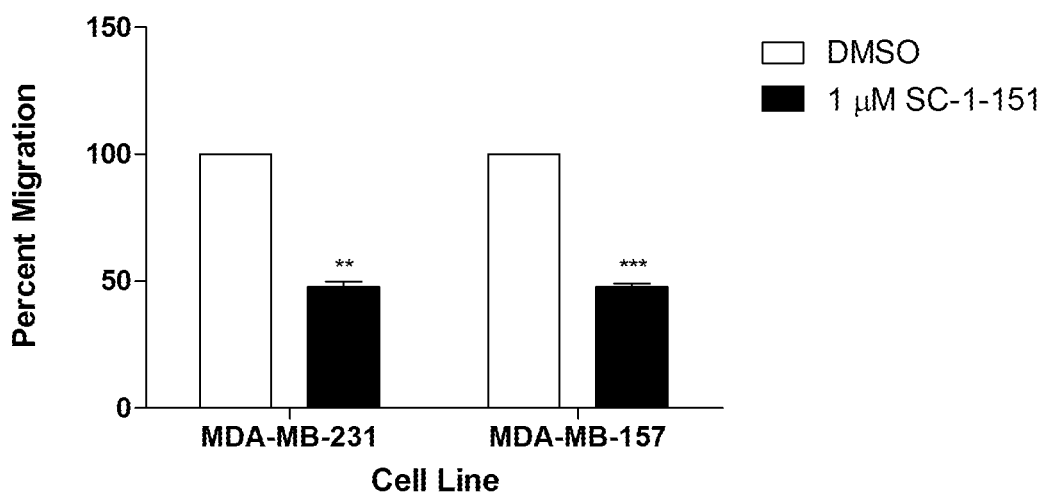
FIG. 18 is a bar graph showing that SC-1-151 decreases migration of triple-negative breast cancer cells. MDA-MB-231 or MDA-MB-157 cells were cultured in 5% CS phenol free DMEM for 48 hours and treated with SC-1-151 or vehicle for 3 days, $2.5 \times 10^4$ cells were then seeded in a transwell insert. After 24 hours, cells were fixed and stained with crystal violet and the number of migrated cells counted. Bars represent percent control migrated cells per 200× field of view±SEM. * $p<0.05$; , $p<0.01$; *, $p<0.001$.
Figure 19:
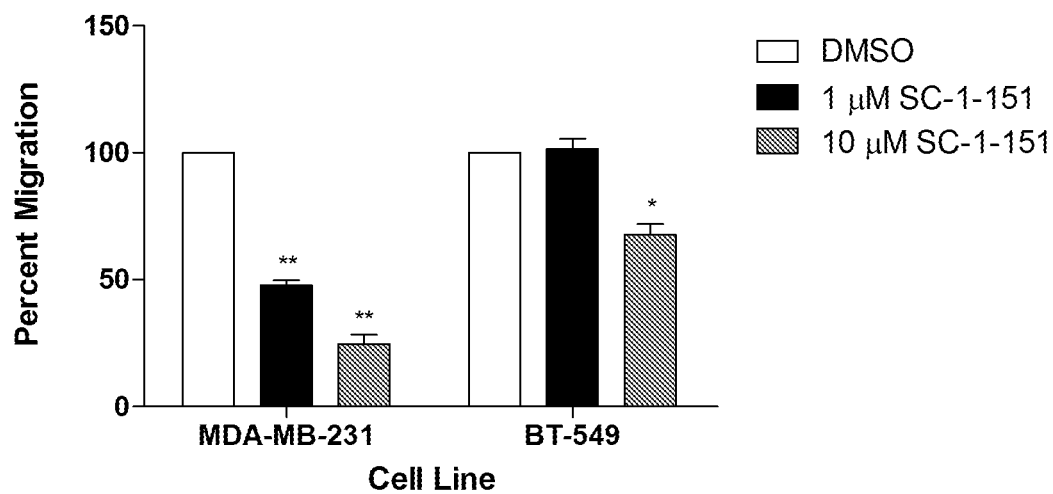
FIG. 19 is a bar graph showing that SC-1-151 decreases migration of triple-negative breast cancer cells. MDA-MB-231 or BT-549 cells were cultured in 5% CS phenol free DMEM for 48 hours and treated with SC-1-151 or vehicle for 3 days, $2.5 \times 10^4$ cells were then seeded in a transwell insert. After 24 hours, cells were fixed and stained with crystal violet and the number of migrated cells counted. Bars represent percent control migrated cells per 200× field of view±SEM. * p<0.05; , p<0.01; *, p<0.001.
Figure 20:
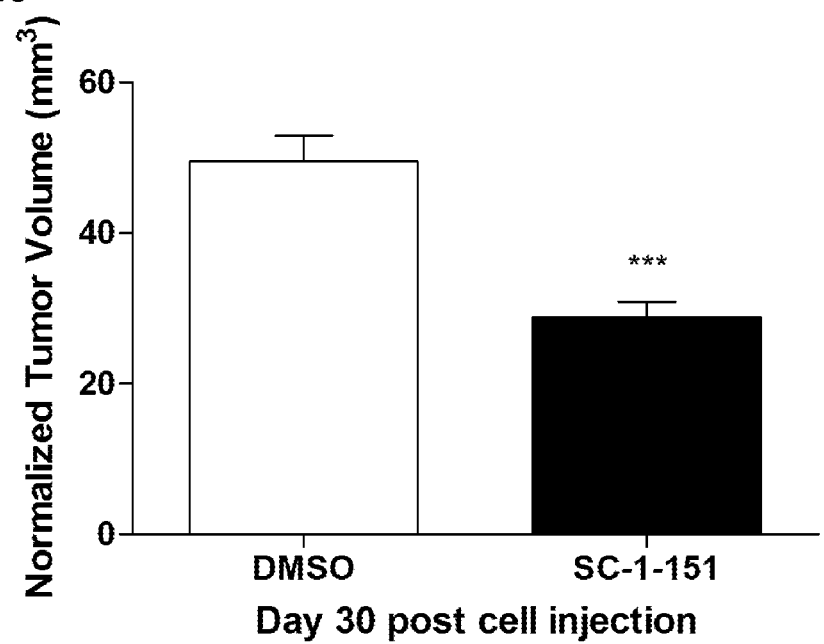
FIG. 20 is a bargraph showing that SC-1-151 decreases tumorigenesis in vivo. End point tumor volume for SCID female mice injected bilaterally with 1×10$^6$ MDA-MB231 cells, n=10. Animals were treated on day 0 (cell injection day) with either DMSO or SC-1-151 (25 mg/kg). Tumor size was measured biweekly for 30 days using a digital caliper. Bars represent final average tumor volume±SEM.
Figure 21:
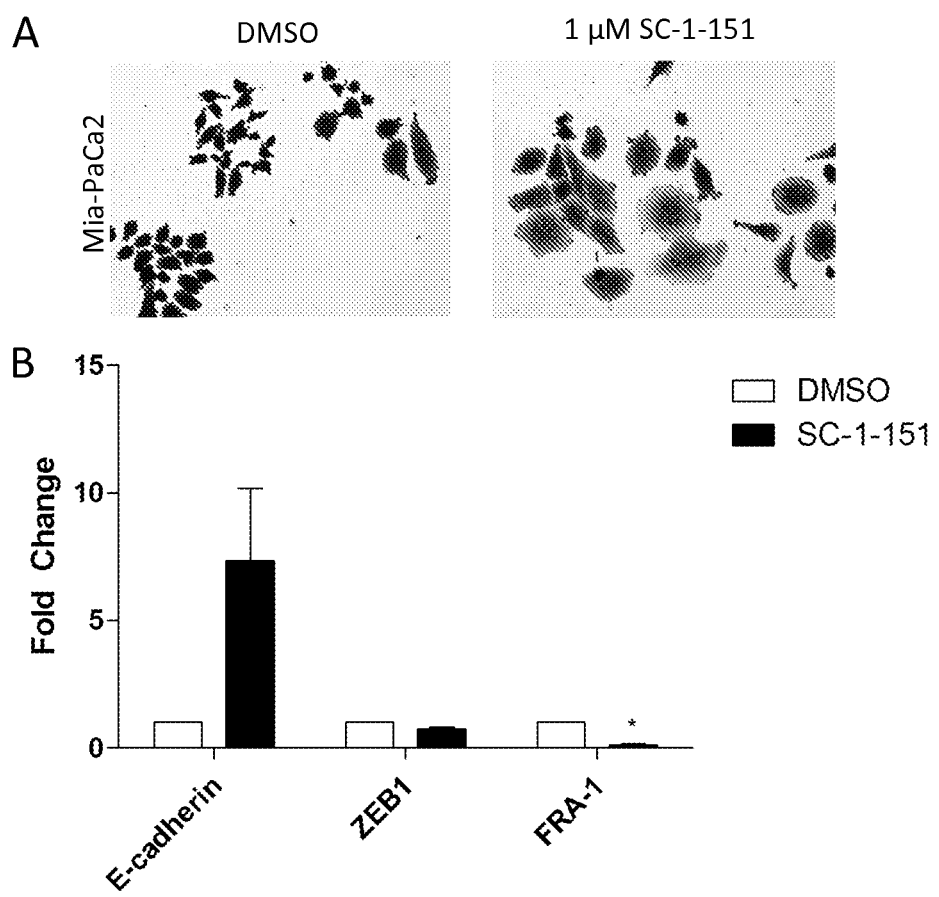
FIGS. 21A and 21B are digital images and a bargraph showing that SC-1-151 induces an epithelial phenotype in pancreatic cancer cells. (A) Mia-PaCa2 cells were seeded in a 96-well plate at a density of 1,000 cells per well and treated with vehicle (DMSO) and SC-1-151. After 3 days, cells were fixed with glutaraldehyde and stained with crystal violet. (B) qPCR for EMT-regulating genes following SC-1-151 treatment. Pancreatic cancer cells were grown in 5% CS phenol free DMEM for 48 hours before treatment with vehicle (DMSO) or SC-1-151 (1 µM) for 24 hours. Cycle number was normalized to R-actin and vehicle-treated cells scaled to 1, n=3.

Proliferation studies were conducted using MDA-MB 231 cells, as they express the triple negative cancer phenotype. Compound 3 was selected due to its potency in inhibition of both MEK1/2 and MEK5. MDA-MB 231 cells were plated at 10,000 cells per well in a 96 well TC plate in 5% Charcoal-Dextran stripped media and incubated overnight at 37° C. in 5% $CO_2$. The cells were treated with drug or vehicle the following day. Plates were harvested on days 3, 5 and 7 and stained with Crystal Violet. Cells were observed for morphological changes under an inverted microscope. The cells were washed, lysed, and the absorbance of Crystal Violet sequestered in living cells was determined at 630 nM. Wells were conducted in duplicate. Experiments were run in triplicate. Cells were normalized to initial cell count. Results are shown in FIG. 11.

The proliferation studies demonstrated that there is a dose-response effect with compound 3. At the 7 day time point, there is a 70% reduction in growth relative to untreated (DMSO). No overt cell death from compound 3 was apparent, even at saturation concentrations.

Examination of the MDA-MB 231 cells during the proliferation testing period was conducted. Untreated (DMSO) cells retained an elongated spiky cellular morphology characteristic of the mobile and invasive mesenchymal phenotype. Treatment of the cells with 1 µM of compound 3 produced an observable alteration of the phenotype in the majority of cells. This treatment concentration suppressed proliferation. Treatment at higher levels with compound 3 (10 µM) had a marked conversion of nearly all cells back to a more rounded phenotype representative of a less mobile, less invasive epithelial phenotype. The observed phenotypic conversion persisted for 14 days without reversion back to the mesenchymal phenotype, see FIG. 12.

Table 2 identifies five of the most active or potent compounds.

TABLE 2

Identification of several potent compounds by Table 1 Registration ID and IUPAC name.

| Structure | Compound Reference | IUPAC Name |
|---|---|---|
| (structure) | SC-1-175 | 3,4-difluoro-2-(phenylamino)benzoic acid |
| (structure) | SC-2-25, Compound 13, Compound 68 | 3,4-difluoro-2-((2-fluorophenyl)amino)benzoic acid |
| (structure) | IC-3-99, Compound 3, IC-D-122a, SC-1-151/ SC-1-172/ SC-2-30, Compound 57 | 3,4-difluoro-2-((2-fluoro-4-iodophenyl)amino)benzamide |
| (structure) | IC-3-95 | (3,4-difluoro-2-((2-fluoro-4-iodophenyl)amino)phenyl)(4-methylpiperazin-1-yl)methanone |
| (structure) | SC-1-148, Compound 7, SC-1-180, Compound 39 | 3,4-difluoro-2-((2-fluoro-4-iodophenyl)amino)benzoic acid |

Taken together, these results show that the compounds disclosed herein provide compositions for and a method of treatment and/or prevention for various cancers, particularly those in which MEK5 is overexpress or significantly up-regulated. These compounds may also provide compositions for and a method of treatment and/or prevention for other diseases which involve or implicate the MEK1/2 and/or MEK5 signaling pathways.

Example 2

Synthetic Methods

All solvents and reagents were used as received unless noted otherwise. All reactions were conducted in dry glassware and under an atmosphere of argon unless otherwise noted. Microwave reactions were conducted in sealed tube and utilized a multimode Milestone Start apparatus for irradiation with power and control parameters as noted. Melting points were determined on a MelTemp apparatus and are uncorrected. All proton NMR spectra were obtained with a 500 MHz or a 400 MHz Oxford spectrospin cryostat, controlled by a Bruker Avance system, and were acquired using Bruker TOPSPIN 2.0 acquisition software. Acquired FIDs were analyzed using MestReC 3.2. Elemental analyses were conducted by Atlantic Microlabs and are ±0.4 of theoretical. All $^1$H NMR spectra were taken in $CDCl_3$ unless otherwise noted and are reported as ppm relative to TMS as an internal standard. Coupling values are reported in Hertz. All TLCs were obtained on Sorbent Technologies polyester backed Silica G TLC Plates of thickness 200 m.

General Method A:

3,4-difluoro-2-((2-fluoro-4-iodophenyl)amino)benzoic acid (SC-1-180) (39). A 250 mL round bottom flask was charged with 2-fluoro-4-iodoaniline, (38; 2.38 g, 10.0 mmol), 2,3,4-trifluorobenzoic acid, (37; 1.80 g, 10.2 mmol), and 30 mL of anhydrous THF. The reaction mixture was cooled with an ice-bath to 0° C. and $LiNH_2$ (561.2 mg, 24.45 mmol) was added in 3 portions over 10 min. The reaction was then warmed to an internal temperature of 58° C. and stirred for 12 h. The mixture was cooled to 0° C. and 1 N HCl was added maintaining the reaction mixture at 0° C. to yield a final pH of 1.0 (red to pHydrion paper). The reaction mixture was then extracted three times with 10 mL portions of $Et_2O$, washed three times with 5 mL portions of 1 N HCl, washed with NaCl (aq, sat), and dried over $Na_2SO_4$. The extract was decanted and the solvent was removed under reduced pressure. The crude product was isolated on $SiO_2$ using 2:1 hexane/EA to provide 2.11 g (53%) of a white solid. MP=199.0-200.1° C. (lit. MP=200-201° C.). $SiO_2$ TLC $R_f$ 0.51 (2:1 hexane/EA). $^1$H NMR (400 MHz, MeOD-$d_4$): δ 6.74 (m, 1H, Ar), 6.91 (m, 1H, Ar), 7.38-7.45 (d, 1H, J=8.5 Hz, Ar), 7.47 (dd, 1H, $J_1$=1.8 Hz and $J_2$=10.5 Hz, Ar), 7.89 (br, 1H, Ar). Anal Calcd for $C_{13}H_7F_3INO_2$: C, 39.72; H, 1.79; N, 3.56. Found: C, 39.41; H, 1.91; N, 3.52.

General Procedure B: Acid Chloride Approach to Synthesize Amide:

A dry 100 mL round bottomed flask was charged with 3,4-difluoro-2-((2-fluoro-4-iodophenyl)amino)benzoic acid, (39) and 5 mL of DCM. The reaction mixture was cooled with an ice-bath to 0° C. 100 μL of anhydrous DMF was added followed by dropwise addition of neat oxalyl chloride (2 equiv.) over 5 min. The reaction was stirred at 23° C. for 4 h. The solvent was then removed under reduced pressure. Excess oxalyl chloride was azeotropically removed with 2×5 mL portions of DCM under reduced pressure. The crude product was dissolved into 5 mL of DCM and the appropriate amine was added neat at 0° C. The ice bath was removed after 10 min and the reaction was permitted to warm to room temperature. The reaction was then stirred at 23° C. for 6 h; completion of reaction was determined by TLC. A mixture of 10 mL of $H_2O$ and 10 mL of $Et_2O$ was added and the resultant mixture was extracted with $Et_2O$, washed with NaCl (aq, sat), and dried over $Na_2SO_4$. The extract was decanted and then the solvent was removed under reduced pressure. The crude product was isolated on $SiO_2$ using hexane/EA.

3,4-difluoro-2-((2-fluoro-4-iodophenyl)amino)benzamide (SC-1-151) (57): was synthesized using procedure B from 3,4-difluoro-2-((2-fluoro-4-iodophenyl)amino)benzoic acid, (39; 1.2 g, 3.0 mmol) and 7 N $NH_3$ in methanol (2 mL, 15.73 mmol). The crude product was isolated on $SiO_2$ using 2:1 hexane/EA to give 900 mg (73%) of a pink-white powder. MP=160.9-162.0° C. $SiO_2$ TLC Rf 0.29 (2:1 hexane/EA). $^1$H NMR (400 MHz, $CDCl_3$): δ 5.72-6.22 (br. d, 2H, $NH_2$), 6.60-6.64 (m, 1H, NH), 6.85-6.90 (m, 1H, Ar), 7.34 (d, 1H, J=8.5 Hz, Ar), 7.39-7.43 (m, 2H, Ar), 8.71 (s, 1H, Ar). Anal Calcd for $C_{13}H_8F_3IN_2O$: C, 39.82; H, 2.06; N, 7.14. Found: C, 39.86; H, 2.18; N, 7.24.

N,N-diethyl-3,4-difluoro-2-((2-fluoro-4-iodophenyl) amino)benzamide (SC-1-65) (59): Compound 59 was synthesized using procedure B (acid chloride approach) from 3,4-difluoro-2-((2-fluoro-4-iodophenyl)amino)benzoic acid, (39; 200 mg, 0.51 mmol) and diethyl amine (0.16 mL, 1.53 mmol). The crude product was isolated on $SiO_2$ using 1:1 hexane/EA and recrystallised from hexanes to give 100.2 mg (45%) of a white solid. MP=78.9-80.1° C. $SiO_2$ TLC Rf 0.7 (1:1 hexane/EA). $^1$H NMR (400 MHz, $CDCl_3$): δ 1.07 (br, 6H), 3.22-3.46 (br. d, 4H, 2N—$CH_2$), 6.50 (s, 1H, NH) 6.51-6.55 (m, 1H, Ar), 6.9-7.04 (m, 2H, Ar), 7.27-7.29 (d, 1H, J=8.5 Hz, Ar), 7.34-7.37 (dd, 1H, $J_1$=1.9 Hz and $J_2$=10.5 Hz, Ar). Anal Calcd for $C_{17}H_{16}F_3IN_2O$: C, 45.5; H, 3.60; N, 6.25; F, 12.72; I, 28.31. Found: C, 45.25; H, 3.57; N, 6.25; F, 12.86; I, 28.22.

3,4-difluoro-2-((2-fluoro-4-iodophenyl)amino)-N,N-dimethylbenzamide (SC-1-69) (58): Compound 58 was synthesized using procedure B from 3,4-difluoro-2-((2-fluoro-4-iodophenyl)amino)benzoic acid, (39; 200.0 mg, 0.51 mmol) and dimethyl amine HCl (408 mg, 5.0 mmol). A solution of dimethyl amine HCl in 5 mL $H_2O$ was added with dropwise addition to a suspension of $Na_2CO_3$ (7 mmol), $H_2O$ (5 mL), DCM (25 mL), and DMAP (5.0 mg, 0.04 mmol) at 0° C. The solution of acid chloride in DCM was added over 5 min and the reaction was stirred at 23° C. for 2 h. A mixture of 10 mL of $H_2O$ and 50 mL of DCM was added and the resultant mixture was washed with $H_2O$ (2×10 mL), washed with NaCl (aq, sat), and then dried over $Na_2SO_4$. The crude product was isolated on $SiO_2$ using 2:1 hexane/EA to give 47 mg (22%) of a white solid. MP=115.4-117.7° C. $SiO_2$ TLC Rf 0.61 (2:1 hexane/EA). $^1$H NMR (400 MHz, $CDCl_3$): δ 2.96 (br, 3H, $CH_3$), 2.91 (br, 3H, $CH_3$), 6.53-6.59 (m, 1H, Ar), 6.82 (s, 1H, NH), 6.91-6.95 (m, 1H, Ar), 7.02-7.06 (m, 1H, Ar), 7.29-7.31 (d, 1H, J=8.5 Hz, Ar), 7.36-7.39 (dd, 1H, $J_1$=1.9 Hz and $J_2$=10.4 Hz, Ar). Anal Calcd for $C_{15}H_{12}F_3IN_2O$: C, 42.8; H, 2.8; N, 6.67; F, 13.5; I, 30.2. Found: C, 42.69; H, 2.89; N, 6.53; F, 13.45; I, 29.99.

3,4-difluoro-2-((2-fluoro-4-iodophenyl)amino)-N-methylbenzamide (SC-1-72 amide) (60): was synthesized using procedure B from 3,4-difluoro-2-((2-fluoro-4-iodophenyl) amino)benzoic acid, (39; 315 mg, 0.8 mmol) and methylamine in methanol (0.5 mL, 4 mmol, 8 M solution). The crude product was isolated on $SiO_2$ using 5:1 hexane/EA and recrystallized from hot EtOH to give 203 mg (63%) of a white solid. MP=159.0-160.2° C. $SiO_2$ TLC Rf 0.51 (1:1 hexane/EA). $^1$H NMR (500 MHz, $CDCl_3$): δ 2.95 (d, 3H, J=4.8 Hz), 6.23 (br, 1H, NH), 6.54-6.59 (m, 1H, Ar), 6.82-6.88 (m, 1H, Ar), 7.28-7.32 (m, 2H, Ar), 7.40 (dd, 1H, J=1.9 Hz and J=10.3 Hz, Ar), 8.61 (s, 1H, NH). Anal Calcd for $C_{14}H_{10}F_3IN_2O$: C, 41.40; H, 2.48; N, 6.90; F, 14.03; I, 31.25. Found: C, 41.67; H, 2.51; N, 6.79; F, 13.79; I, 31.35.

Methyl 3,4-difluoro-2-((2-fluoro-4-iodophenyl)amino) benzoate (SC-1-72 ester) (62): was obtained as a side-product using procedure B during the synthesis of 60 from 3,4-difluoro-2-((2-fluoro-4-iodophenyl)amino)benzoic acid, (39; 315 mg, 0.8 mmol) and methylamine in methanol (0.5 mL, 4 mmol, 8 M solution). The product was obtained as 60 mg (17%) of a white solid. MP=118.5-111.4° C. $SiO_2$ TLC Rf 0.82 (2:1 hexane/EA). $^1$H NMR (400 MHz, CDCl3): δ 3.91 (s, 3H), 6.65-6.71 (m, 1H, Ar), 6.74-6.80 (m, 1H, Ar), 7.35 (d, 1H, J=8.6 Hz), 7.42 (dd, 1H, J=1.9 Hz and J=10.2 Hz, Ar), 7.78-7.82 (m, 1H, Ar), 9.04 (s, 1H, NH). Anal Calcd for $C_{14}H_9F_3INO_2$: C, 41.30; H, 2.23; N, 3.44; F, 14.00; I, 31.17. Found: C, 41.43; H, 2.08; N, 3.52; F, 14.18; I, 31.31.

Tert-butyl 4-(3,4-difluoro-2-((2-fluoro-4-iodophenyl) amino)benzoyl)piperazine-1-carboxylate (SC-1-75) (64): Compound 64 was synthesized using procedure B from 3,4-difluoro-2-((2-fluoro-4-iodophenyl)amino)benzoic acid, (39; 1.00 g, 2.54 mmol) and N-Boc-piperazine (2.85 g, 5.08 mmol). A solution of acid chloride in 6 mL DCM was added with dropwise addition to a solution of N-Boc-piperazine, TEA (0.70 mL, 5.08 mmol), DCM (12 mL) and DMAP (5.0 mg, 0.04 mmol) at 0° C. and the reaction was stirred at 23° C. for 2 h. The crude product was isolated on $SiO_2$ using 2:1 hexane/EA to give 630 mg (44%) of a white solid. MP=188.4° C. $SiO_2$ TLC Rf 0.5 (1:1 hexane/EA). $^1$H NMR (400 MHz, $CDCl_3$): δ 1.45 (s, 9H), 3.34-3.55 (m, 8H), 6.53-6.58 (m, 1H, Ar), 6.62 (s, 1H, NH), 6.92-6.96 (m, 1H, Ar), 7.03 (m, 1H, Ar), 7.30 (d, 1H, J=8.9 Hz, Ar), 7.39 (dd, 1H, J=1.9 Hz and J=10.4 Hz, Ar). Anal Calcd for $C_{22}H_{23}F_3IN_3O_3$: C, 47.07; H, 4.13; N, 7.49; F, 10.15; I, 22.61. Found: C, 47.22; H, 4.18; N, 7.40; F, 9.94; I, 22.64.

(3,4-difluoro-2-((2-fluoro-4-iodophenyl)amino)phenyl) (piperazin-1-yl)methanone hydrochloride (SC-1-79) (63): was synthesized from 64 (530 mg, 0.94 mmol) and 1:1 15 mL (v/v) HCl/Dioxane. A solution of 64 was taken in a 250 mL RBF and 15 mL of 1:1 conc. HCl in Dioxane was added with constant stirring at 23° C. for 3.5 hrs. The crude product was recrystallized from hot EtOH to give 340 mg (79%) of a white solid; MP=201.2-203.6° C. $^1$H NMR (400 MHz, MeOD-$d_4$): δ 3.08 (br, 4H), 3.60 (m, 4H), 6.58-6.62 (t, 1H, Ar), 7.12-7.22 (m, 2H, Ar), 7.32 (d, 1H, J=8.5 Hz, Ar) 7.46 (dd, 1H, J=1.9 Hz and J=10.8 Hz, Ar). Anal Calcd for $C_{17}H_{15}F_3IN_3O$: C, 41.03; H, 3.24; N, 8.44; F, 11.45; I, 25.50. Found: C, 40.77; H, 3.38; N, 8.34; F, 11.20; I, 25.24.

N-ethyl-3,4-difluoro-2-((2-fluoro-4-iodophenyl)amino) benzamide (SC-1-80) (61): was synthesized using procedure B from 3,4-difluoro-2-((2-fluoro-4-iodophenyl)amino)benzoic acid, (39; 315 mg, 0.8 mmol) and ethyl amine 2M solution in THF (2.25 mL, 4.5 mmol). The crude product was isolated on $SiO_2$ using 2:1 hexane/EA and recrystallized from hot EtOH to give 155 mg (41%) of a white solid. MP=172.5-173.6° C. SiO2 TLC R_f_ 0.7 (2:1 hexane/EA). $^1$H NMR (400 MHz, $CDCl_3$): δ 1.19 (t, 3H, J=7.3 Hz), 3.38-3.45 (m, 2H), 6.22 (br, 1H, NH), 6.54-6.59 (m, 1H, Ar), 6.82-6.89 (m, 1H, Ar), 7.31 (m, 2H, Ar), 7.40 (dd, 1H, J=2.0 Hz, J=10.3 Hz, Ar), 8.52 (s, 1H, NH). Anal Calcd for $C_{15}H_{12}F_3IN_2O$: C, 42.88; H, 2.88; N, 6.67; F, 13.56; I, 30.20. Found: C, 42.89; H, 2.89; N, 6.60; F, 13.57; I, 30.47.

N-(2-(dimethylamino)ethyl)-3,4-difluoro-2-((2-fluoro-4-iodophenyl)amino)-N-methylbenzamide hydrochloride (SC-1-122) (65): was synthesized using procedure B from 3,4-difluoro-2-((2-fluoro-4-iodophenyl)amino)benzoic acid, (39; 360 mg, 0.88 mmol) and N,N,N'-trimethylethane-1,2-diamine (0.34 ml, 2.64 mmol). A solution of N,N,N'-trimethylethane-1,2-diamine (0.34 ml, 2.64 mmol), TEA (0.37 mL, 2.64 mmol) and DMAP (6 mg, 0.05 mmol) in 3 mL DCM was added dropwise to a solution of the acid chloride in DCM over 5 min and the reaction was stirred at 23° C. for 12 h. The crude product was isolated on $SiO_2$ using $CHCl_3$ and 5% MeOH to give 290 mg. HCl salt was made from ethereal HCl and recrystallized from hot ethanol to afford 168.2 mg (40%) of a white solid. MP=211-213° C. $SiO_2$ TLC Rf 0.7 (DCM/5% MeOH/0.1% $NH_4OH$). $^1H$ NMR (500 MHz, DMSO-d6): δ 2.78 (s, 6H, $2CH_3$), 2.84 (s, 3H, $CH_3$), 3.13 (m, 2H, $CH_2$), 3.61 (t, 2H, CH2), 6.59-6.63 (t, 1H, Ar), 7.27-7.33 (m, 2H, Ar), 7.52-7.53 (dd, 1H, J=1.6 Hz, J=11.3 Hz, Ar), 8.05 (s, 1H, Ar), 10.06 (s, 1H, NH). Anal Calcd for $C_{18}H_{20}ClF_3IN_3O$: C, 42.08; H, 3.92; N, 8.18; F, 11.09; I, 24.70. Found: C, 42.21; H, 3.98; N, 8.09; F, 11.22; I, 24.52.

Procedure C (Ullmann Coupling):

2-((2-fluoro-4-iodophenyl)amino)benzoic acid (SC-1-14) (98): A microwave reactor tube was charged with ortho-iodo benzoic acid (496 mg, 2 mmol), 2-fluoro-4-iodo aniline (237 mg, 1 mmol), $K_2CO_3$ (416 mg, 3 mmol), CuI (200 mg, 1.04 mmol) and 5 mL DMF/H2O (9:1). The reaction was subjected to 300 Watt microwave irradiation with the internal temperature maintained at 100° C. for 2 h. After completion of the reaction was analyzed by TLC, 1 N HCl (~4 mL) was added to the reaction mixture to obtain a final solution pH of 6.0. The solvent was then removed under reduced pressure. The crude compound was isolated on $SiO_2$ using 1:1 hexane/EA to give 217 mg (61%) of white solid; MP=186.2-186.5° C. $SiO_2$ TLC Rf 0.70 (1:1 hexane/EA). $^1H$ NMR (400 MHz, $CDCl_3$): δ 6.85 (t, 1H, J=7.1 Hz, Ar), 7.11 (d, 1H, J=8.6 Hz, Ar), 7.20 (t, 1H, J=8.4 Hz, Ar), 7.42 (m, 2H, Ar), 7.50 (dd, 1H, J=2.0 Hz and J=9.8 Hz, Ar), 8.06 (dd, 1H, J=1.6 Hz and J=8.1 Hz, Ar), 9.25 (s, 1H, $CO_2H$). Anal Calcd for $C_{13}H_9FINO_2$: C, 43.72; H, 2.54; N, 3.92. Found: C, 43.81; H, 2.65; N, 3.80.

(2-((2-fluoro-4-iodophenyl)amino)phenyl)(4-methylpiperazin-1-yl)methanone hydrochloride (SC-1-24) (74): A dry 100 mL round bottom flask was charged with 98, (140 mg, 0.39 mmol) and 5 mL of DCM. The reaction mixture was cooled on ice-bath to 0° C. 100 μL of anhydrous DMF was added followed by dropwise addition of oxalyl chloride (70 μL, 0.8 mmol) over 2 min at 0° C. The reaction was stirred at 23° C. for 2 h. The solvent was then removed under reduced pressure. The crude product was dissolved into 5 mL of DCM and N-methyl piperazine (0.5 mL, 4.5 mmol) was added neat at 23° C. The reaction was stirred at 23° C. for 2 h; completion of reaction was determined by TLC. A mixture of 10 mL of DCM and 5 mL of 5% $Na_2CO_3$ was added and the resultant mixture was extracted with DCM, washed with NaCl (aq, sat), and dried over $Na_2SO_4$. The extract was decanted and then the solvent was removed under reduced pressure and water chased with toluene. The crude product was isolated on $SiO_2$ using EA/0.5% TEA/10% ethanol and recrystallised from HCl salt (ethereal HCl) to give 20 mg (12%) of off-white powder. MP=217.2-217.5° C. $SiO_2$ TLC Rf 0.24 (20% EA/EtOH). $^1H$ NMR (400 MHz, MeOD-d4): δ 1.18 (t, 4H, J=7.0 Hz), 2.89 (s, 3H), 3.49 (q, 2H, J=7.0 Hz), 3.60 (q, 2H, J=7.1 Hz), 6.92 (t, 1H, J=8.7 Hz), 7.09 (t, 1H, J=7.5 Hz), 7.15 (d, 1H, J=8.2 Hz), 7.34-7.42 (m, 3H), 7.49 (dd, 1H, J=2.0 Hz and J=10.7 Hz). Anal Calcd for $C_{18}H_{20}ClFIN_3O$. 0.38% EtOH: C, 45.68; H, 4.55; N, 8.51; F, 3.85; I, 25.71; Cl, 7.18. Found: C, 45.9; H, 4.49; N, 8.54; F, 3.66; I, 25.68; Cl, 7.49.

2-(phenylamino)benzoic acid (SC-1-39) (25): A microwave reactor tube was charged with ortho-iodo benzoic acid (496 mg, 2 mmol), aniline (24) (0.45 mL, 4 mmol), $K_2CO_3$ (832 mg, 6 mmol), CuI (400 mg, 2.08 mmol) and 10 mL DMF/H2O (9:1). The reaction was subjected to 300 Watt microwave irradiation with the internal temperature maintained at 100° C. for 1 h. After completion of the reaction was observed by TLC, 1 N HCl (~9 mL) was added to the reaction mixture to obtain a final pH of 6.0. The solvent was then removed under reduced pressure and water was azeotropically removed with 3×10 mL of toluene. The crude compound was isolated on $SiO_2$ using hexane/EA and recrystallised from toluene to give 267 mg (63%) of white solid; MP=176.6-177.0° C. $^1H$ NMR (400 MHz, $CDCl_3$): δ 6.76 (t, 1H, J=7.5 Hz, Ar), 7.13 (t, 1H, J=7.3 Hz, Ar), 7.23 (d, 1H, J=8.7 Hz, Ar), 7.26-7.28 (m, 2H, Ar), 7.33-7.39 (m, 3H, Ar), 8.04 (dd, 1H, J=1.6 Hz and J=8.1 Hz, Ar), 9.33 (s, 1H, $CO_2H$).

Procedure D (DIC Coupling)

(4-methylpiperazin-1-yl)(2-(phenylamino)phenyl)methanone (SC-1-177 amide) (75): A dry 100 mL round bottom flask was charged with 25, (1.00 g, 4.69 mmol) and 12 mL of DCM. N-methyl piperazine (2.59 mL, 23.45 mmol) and DMAP (9 mg, 0.07 mmol) was added followed by DIC (1.08 mL, 7 mmol) and the reaction mixture was stirred at 23° C. for 22 h. The solvent was removed under reduced pressure. A mixture of 10 mL of ether and HCl was added and the resultant mixture was extracted into HCl (3×5 mL) and washed with ether (2×5 mL). The aqueous layer was basified with 5% $Na_2CO_3$ and the crude material was extracted into DCM (3×8 mL). The crude product was loaded onto $SiO_2$ and eluted with chloroform: methanol (95:5). Collection of appropriate fractions, removal of solvent, and recrystallization from hot ethanol gave 232 mg (17%) of transparent colorless needles. MP=105.9-108.0° C. $SiO_2$ TLC Rf 0.35 (chloroform/1% methanol). $^1H$ NMR (400 MHz, MeOD-d4): δ 2.23 (s, 3H, $CH_3$), 2.35 (br, 4H, $2CH_2$), 3.73-3.82 (m, 4H, $2CH_2$), 6.88 (t, 1H, J=7.3 Hz), 6.97-7.01 (m, 3H, Ar), 7.19-7.26 (m, 4H, Ar), 7.30-7.34 (m, 1H, Ar). Anal Calcd for $C_{18}H_{21}N_3O$: C, 73.19; H, 7.17; N, 14.23. Found: C, 73.14; H, 7.22; N, 14.23.

3,4-difluoro-2-(phenylamino)benzoic acid (SC-1-175 acid) (71): A 250 mL round bottom flask was charged with aniline (24) (0.57 mL, 5.7 mmol), 2,3,4-trifluorobenzoic acid (37), (1 g, 5.7 mmol), and 15 mL of anhydrous THF. The reaction mixture was cooled with an ice-bath to 0° C. and $LiNH_2$ (327 mg, 14.25 mmol) was added in portions 2 portions over 10 min. The reaction was then warmed to 58° C. (external temperature) and stirred for 7 h. 1 N HCl was then added to the reaction mixture at 0° C. to obtain a final pH of 1.0 (red to pHydrion paper). The reaction mixture was extracted three times with 5 mL portions of $Et_2O$, washed three times with 5 mL portions of 1 N HCl, washed with NaCl (aq, sat) and dried over $Na_2SO_4$. The extract was decanted and the solvent was removed under reduced pressure. The crude product was isolated on $SiO_2$ using hexane/EA and provided 606 mg (44%) yellow crystals. MP=162.1-162.6° C. $SiO_2$ TLC Rf 0.61 (2:1 hexane/EA). $^1H$ NMR (500 MHz, $CDCl_3$): δ 6.73-6.78 (m, 1H, Ar), 7.05 (d, 2H, J=7.5 Hz, Ar), 7.10 (t, 1H, J=7.4 Hz), 7.32 (t, 2H, J=7.6 Hz), 7.87-7.90 (m, 1H, Ar), 8.99 (s, 1H, OH).

Procedure E (EDCI Coupling)

3,4-difluoro-2-(phenylamino)phenyl)(4-methylpiperazin-1-yl)methanone (SC-1-181) (72): A solution of 71 (249 mg, 1 mmol), N-methyl piperazine (0.25 mL, 2 mmol) and DMAP (6 mg, 0.05 mmol) was prepared in 10 mL anhydrous THF, then EDCI (382 mg, 2 mmol) was added in one portion. The reaction mixture was stirred at 23° C. for 12 hrs. The solvent was removed under reduced pressure and a mixture of 50 mL of ether and 1 mL $H_2O$ was added. The resultant mixture was washed three times with 1 mL portions of $H_2O$, 5 mL of saturated NaCl and then dried over anhydrous $Na_2SO_4$. The crude product was isolated on $SiO_2$ using CHCl$_3$, 1% MeOH, 1% TEA to give 204 mg (62%) of a white solid. MP=153.0-155.3° C. $^1$H NMR (400 MHz, CDCl$_3$): δ 2.22 (s, 4H, 2CH$_2$), 2.27 (br, 3H, CH$_3$), 3.47 (br, 4H, 2CH$_2$), 3.57 (br, 4H, NH), 6.82-6.95 (m, 4H, Ar), 6.99-7.03 (m, 1H, Ar), 7.22-7.24 (m, 2H, Ar). Anal Calcd for C$_{18}$H$_{19}$F$_2$N$_3$O: C, 65.24; H, 5.78; N, 12.68; F, 11.47. Found: C, 65.38; H, 5.89; N, 12.72; F, 11.46.

3,4-difluoro-2-((2-fluorophenyl)amino)benzoic acid (SC-2-25 acid) (68): A 100 mL dry round bottom flask was charged with 2-fluoroaniline (0.27 mL, 2.97 mmol), 2,3,4-trifluorobenzoic acid, (528 mg, 3 mmol), and 7 mL of anhydrous THF. The reaction mixture was cooled with an ice-bath to 0° C. and LiNH$_2$ (165.2 mg, 7.2 mmol) was added in 2 portions over a 10 min interval. The reaction was then warmed to 58° C. (external temperature) and stirred for 4 h. 1 N HCl was then added to the reaction mixture at 0° C. to obtain a final pH of 1.0 (red to pHydrion paper). The reaction mixture was extracted three times with 5 mL portions of Et$_2$O, washed three times with 5 mL portions of 1 N HCl, washed with NaCl (aq, sat), and dried over Na$_2$SO$_4$. The extract was decanted and the solvent was removed under reduced pressure. The crude product was isolated on SiO$_2$ using hexane/EA to provide 471 mg (59%) of white crystals. MP=170-172° C. SiO$_2$ TLC Rf 0.55 (2:1 hexane/EA). $^1$H NMR (400 MHz, CDCl$_3$): δ 6.72-6.78 (dt, 1H, J=6.8 Hz and J=9.1 Hz, Ar), 7.00-7.13 (m, 4H, Ar), 7.87-7.91 (ddd, 1H, J=2.1 Hz, J=5.8 Hz and J=9.1 Hz, Ar), 8.92 (s, 1H, CO$_2$H). Anal Calcd for C$_{13}$H$_8$F$_3$NO$_2$: C, 58.44; H, 3.02; N, 5.24. Found: C, 58.41; H, 3.02; N, 5.23.

(3,4-difluoro-2-((2-fluorophenyl)amino)phenyl)(4-methylpiperazin-1-yl)methanone mono-fumarate (SC-2-45) (69): was synthesized using procedure E from 68, N-methyl piperazine and EDCI. A solution of 68 (430 mg, 1.61 mmol), N-Methyl piperazine (0.35 mL, 3.22 mmol) and DMAP (6 mg, 0.05 mmol) was prepared in 12 mL anhydrous THF and then EDCI (615 mg, 3.22 mmol) was added. The reaction mixture was stirred at 23° C. for 6 hrs; completion of reaction was followed by TLC. The crude product was isolated on SiO$_2$ using CHCl3, 1% MeOH, 1% TEA. The fumarate salt of the compound was prepared from fumaric acid (186 mg, 1.61 mmol) followed by recrystallization from hot EtOH to give 81 mg (14%) of a white solid. MP=155.0-160° C. SiO$_2$ TLC Rf 0.2 (CHCl$_3$+2% MeOH). $^1$H NMR (400 MHz, CDCl$_3$): δ 2.68 (s, 3H, CH$_3$), 2.83-2.94 (br, 4H, 2CH$_2$), 3.57 (br, 4H, 2CH$_2$), 6.72 (s, 2H, CH=CH), 6.82-6.86 (m, 1H, Ar), 6.89-6.94 (m, 1H, Ar), 6.97-7.01 (m, 1H, Ar), 7.04-7.12 (m, 2H, Ar), 7.14-7.18 (m, 1H, Ar). Anal Calcd for C$_{22}$H$_{22}$F$_3$N$_3$O$_5$. 0.55% Fumaric acid. 0.78% EA: C, 54.87; H, 5.13; N, 7.02. Found: C, 54.98; H, 4.88; N, 6.86.

3,4-difluoro-2-((2-fluorophenyl)amino)benzamide (SC-2-37) (70): was synthesized using procedure B from 68, (267 mg, 1 mmol) and 7 N NH$_3$ in methanol (0.65 mL, 5.03 mmol). The crude product was isolated on SiO$_2$ using hexane/EA to give 96 mg (36%) of a white powder. MP=157.6-161.2° C. $^1$H NMR (400 MHz, CDCl$_3$): δ 6.82-6.88 (m, 2H, NH$_2$), 6.91-6.97 (m, 1H, Ar), 6.99-7.10 (m, 3H, Ar), 7.44 (ddd, 1H, J=2.1 Hz, J=5.5 Hz and J=8.8 Hz, Ar), 8.45 (s, 1H, Ar). Anal Calcd for C$_{13}$H$_9$F$_3$N$_2$O: C, 58.65; H, 3.41; N, 10.52; F, 21.41. Found: C, 58.22; H, 3.27; N, 10.20; F, 21.71.

2-fluoro-4-iodo-N-methylaniline (SC-2-20 amine) (108): 2-fluoro-4-iodoaniline (474 mg, 2 mmol) was added to a dry 100 mL round bottom flask containing a suspension of NaOMe (540 mg, 10 mmol) in MeOH (5 mL). This mixture was poured into a suspension of paraformaldehyde (84 mg, 2.8 mmol) in anhydrous MeOH (4 mL) and the reaction mixture was stirred at 25° C. for 5 h. After 5 h, NaBH$_4$ (75 mg, 2 mmol) was added and the reaction mixture was refluxed at 90° C. for 2.5 h. The solvent was evaporated and the reaction mixture was treated with 5 mL 1 M KOH. The product was extracted into diethyl ether (2×8 mL) and dried over Na$_2$SO$_4$. The extract was decanted and the solvent was removed under reduced pressure. The crude product was isolated on SiO$_2$ using 20% EA/hexane to provide 270 mg (54%) of white needles. MP=44° C. SiO$_2$ TLC Rf 0.75 (2:1 hexane/EA). $^1$H NMR (400 MHz, CDCl$_3$): δ 2.85 (d, 3H, J=4.6 Hz), 3.97 (s, 1H, NH), 6.43 (t, 1H, J=8.8 Hz), 7.22-7.26 (m, 1H, Ar), 7.30 (d, 1H, J=9.3 Hz, Ar). Anal Calcd for C$_7$H$_7$FIN: C, 33.39; H, 2.81; N, 5.58. Found: C, 33.69; H, 2.67; N, 5.64.

3,4-difluoro-2-((2-fluoro-4-iodophenyl)(methyl)amino) benzoic acid (SC-2-32) (76): A 100 mL dry round bottom flask was charged with 2-fluoro-4-iodo-N-methylaniline (270 mg, 1.07 mmol), 2,3,4-trifluorobenzoic acid, (192 mg, 1.09 mmol), and 10 mL of anhydrous THF. The reaction mixture was cooled with an ice-bath to 0° C. and LiNH$_2$ (60 mg, 2.6 mmol) was added in portions 2 portions over 5 min. The reaction was then warmed to 58° C. (external temperature) and stirred for 48 h. 1 N HCl was then added to the reaction mixture at 0° C. to obtain a final pH of 1.0 (red to pHydrion paper). The reaction mixture was extracted three times with 5 mL portions of Et2O, washed three times with 5 mL portions of 1 N HCl, washed with NaCl (aq, sat) and dried over Na2SO4. The extract was decanted and the solvent was removed under reduced pressure. The crude product was isolated on SiO$_2$ using 3:1 hexane/EA and recrystallized from toluene and hexanes to provide 286 mg (66%) of brown crystals. MP=86.2-89.1° C. SiO$_2$ TLC Rf 0.45 (2:1 hexane/EA). $^1$H NMR (500 MHz, CDCl$_3$): δ 3.34 (s, 3H), 6.97 (t, 1H, J=8.8 Hz, Ar), 7.24-7.27 (m, 1H, Ar), 7.35-7.37 (dd, 1H, J=2.0 Hz and J=11.4 Hz, Ar), 7.50 (d, 1H, J=8.6 Hz, Ar), 8.07-8.10 (m, 1H, Ar). Anal Calcd for C$_{14}$H$_9$F$_3$INO$_2$. 0.0436% C$_6$H$_5$CH$_3$: C, 41.78; H, 2.29; N, 3.40. Found: C, 41.77; H, 2.42; N, 3.35.

Example 3

Biological Evaluation

Cell Culture and Treatment

MDA-MB-231 cells were grown on 10 cm cell culture plates [Sarstedt] in Dulbecco's Modified Eagle's Medium (DMEM; Gibco) with Ham's F12 Nutrient Mixture (1:1) (Invitrogen), 10% heat-inactivated FBS [Atlanta Biological and 0.5% penicillin/streptomycin [Gibco]. Cells were maintained at 37° C. with 5% CO2. Plating of the cells was done 36 hours before treatment in 35 mm culture plates [Sarstedt] and allowed to reach confluence. To test MEK-5 inhibitors, the cells were treated with epidermal growth factor (EGF; Sigma-Aldrich) 30 min after treatment with the compounds. 15 min after the addition of EGF, the cells were washed with 1×PBS [Sigma-Aldrich] and then lysed in 1% Triton X-100 buffer containing 20 mM Tris (pH 6.8), 137 mM NaCl, 25 mM beta glycerophosphate, 2 mM NaPPi, 2 mM EDTA, 1 mM Na$_3$VO$_4$, 10% glycerol, 5 µg/mL leupeptin, 5 µg/mL aprotinin, 2 mM benzamidine, 0.5 mM DTT, and 1 mM PMSF. The lysates were then centrifuged at 10,000 rpm for 10 min at 4° C.

Western Blot Analysis

Total protein content was assessed by Bradford Bio-Rad protein assay (Cat. No. 500-0006, Bio-Rad, Hercules, Calif.) and 30 µg of protein was loaded on a 8% SDS-PAGE gel for phosphorylated and total ERK1/2 and ERK5 proteins. After running the samples, gels were transferred to a nitrocellulose membrane (Cat. No. 926-31092, Licor Biosciences, Lincoln, Nebr.). After transfer, membranes were washed for 5 min with 1×PBS and blocked for 1 h in a Casein Blocking Buffer (Cat. No. 927-40200, Licor Biosciences) at room temperature. Membranes were then incubated overnight at 4° C. in primary antibody in CBB with 0.2% Tween-20. Antibodies included rabbit anti-phospho-ERK1/2 (Dilution—1:1000, Cat. No. 9101, Cell Signaling, Beverly, Mass.), mouse anti-total ERK1/2 (Dilution—1:1000, Cat. No. 9107, Cell Signaling), and rabbit anti-total ERK5 (Dilution—1:1,000, Cat. No. 3372, Cell Signaling). Mouse anti-α-Tubulin (Dilution—1:10,000, Cat. No. T5168, Sigma-Aldrich) was used as a loading control. After incubation with primary antibody, blots were washed in 1×PBS solution with 0.2% Tween-20 (1×PBS-T) and incubated with goat anti-rabbit (Dilution—1:10,000, Cat. No. 926-68021, LICOR Biosciences) and goat anti-mouse (Dilution—1:10,000, Cat. No. 926-32210, LICOR Biosciences) secondary antibodies for 1 h at room temperature. After washing the membranes with 1×PBS-T, the protein bands were visualized on an Odyssey Infrared Imager and quantified with Odyssey software (LICOR Biosciences).

| Compounds | pERK-5 relative activity (%) | pERK-5 decrease (%) | pERK-½ relative activity (%) | pERK-½ decrease (%) |
|---|---|---|---|---|
| DMSO | 100 | 0 | 100 | 0 |
| SC-1-75 | — | 8.4 | — | 70.9 |
| SC-1-65 | 7.4 | — | — | 5.5 |
| SC-1-24 | — | 30.9 | — | 33.5 |
| SC-1-122 | — | 9.4 | — | 27.9 |
| SC-1-69 | — | 0.2 | — | 87.3 |
| SC-1-72 amide | — | 20.4 | — | 99.6 |
| SC-1-72 ester | — | 13.0 | — | 98.9 |
| SC-1-79 | 6.2 | — | — | 99.0 |
| SC-1-80 | — | 8.5 | — | 98.6 |
| SC-1-177 | — | 71 | — | 29.3 |
| SC-1-181 | — | 82.4 | 8.5 | — |
| SC-1-151 | — | 59 | — | 96.8 |
| SC-1-180 | — | 20.1 | — | 98.5 |
| SC-1-175 | — | 10.4 | — | 7.1 |
| SC-2-25 | — | 11.1 | 7.1 | — |
| SC-2-32 | 5.5 | — | — | 33.5 |
| SC-2-37 | — | 56.1 | — | 52.8 |
| SC-2-45 | — | 40.5 | — | 16.5 |
| U0126 | — | 43 | — | 99.6 |
| XMD8-92 | — | 95.2 | — | 50.1 |
| PD 0325901 | — | 95.9 | — | 99.7 |

Crystal Violet Proliferation Assay

Triple-negative breast cancer (TNBC) cells MDA-MB-231 were seeded in 96-well plates at a density of 2,000 cells per well in 5% charcoal-stripped phenol free DMEM, allowed to attach overnight, and subsequently treated with DMSO and MEK inhibitor compounds in duplicate. Plates were harvested on days 3, 5 and 7, fixed with glutaraldehyde, and stained with crystal violet. Cells were observed for morphological changes under an inverted microscope. Cells were washed, lysed with 33% acetic acid, and the absorbance was read at 630 nm in a Biotek Synergy plate reader. Data are represented as mean cell viability normalized to vehicle treatment±SEM of triplicate experiments with internal duplicates.

Quantitative Real-Time Polymerase Chain Reaction (qPCR)

Cancer cells were grown in 5% charcoal-stripped phenol red free DMEM for 48 hours and treated with compounds (1 µM). After 24 hours, cells were collected and total RNA was extracted using the RNeasy kit, in accordance with the manufacturer's protocol (Qiagen, Germantown, Md.). The quality and concentration of RNA were determined spectrophotometrically by absorbance at 260 and 280 nm. Total RNA (1 µg) was reverse-transcribed using the iScript kit (BioRad, Hercules, Calif.). Cycle number was normalized to (3-actin and vehicle-treated cells scaled to 1, n=3.

Migration Assay

TNBC cells were cultured in 5% CS phenol free DMEM for 48 hours and treated with SC-1-151 or vehicle for 3 days, $2.5 \times 10^4$ cells were then seeded in a transwell insert. After 24 hours, cells were fixed and stained with crystal violet and the number of migrated cells counted. Data are represented as percent control migrated cells per 200× field of view±SEM. Experiments were conducted in triplicate.

Animal Xenograft Study

Immune-compromised SCID/beige female mice (29-32 days old) were obtained from Charles River Laboratories (Wilmington, Mass.). The animals were allowed a period of adaptation in a sterile and pathogen-free environment with food and water ad libitum. Breast cancer cells MDA-MB-231 were grown in 5% FBS charcoal-stripped DMEM for five days then harvested. Viable cells were mixed with PBS and Matrigel Reduced Factors (BD Biosciences, San Jose, Calif.). Injections ($1 \times 10^6$ cells/injection) were made bilaterally into the mammary fat pad on day 0 (May 7, 2013). All the procedures in animals were carried out under anesthesia using a mix of isoflurane and oxygen delivered by mask. Animals were treated on day 0 with either DMSO or SC-1-151 (25 mg/kg). Tumor size was measured biweekly for 30 days using a digital caliper. Tumor volume was calculated using the following formula: $4/3\pi LM^2$, where L is the larger radius and M is the smaller radius. On day 31, tumors were excised and blocked in OCT compound. Mice were monitored daily to insure survival after the surgery. Mice were allowed to proceed for 14 days to examine effects of drug treatment on metastasis.

Statistical Analyses

Statistical analyses were performed using Graphpad Prism software (Graph-Pad Software, Inc., San Diego, Calif.). Data were subjected to unpaired Student's t-test, with $p<0.05$ considered statistically significant Example 4

Treatment of Subjects

This example describes methods that can be used to treat a subject having a particular disease or condition, such as cancers, that can be treated by a disclosed anthranilic amide derivative. Such a therapy can be used alone, or in combination with other therapies (such as the administration of a chemotherapeutic agent).

In particular examples, the method includes screening a subject having or thought to have a particular disease or condition treatable by a disclosed anthranilic amide derivative. Subjects of an unknown disease status or condition can be examined to determine if they have a disease or condition treatable by a disclosed anthranilic amide derivative for example by using the methods described herein.

The subject can be administered a therapeutic amount of a disclosed anthranilic amide derivative. The disclosed anthranilic amide derivative can be administered at doses of 0.0001 µg/kg body weight to about 10 mg/kg body weight per dose, such as 0.0001 µg/kg body weight-0.001 µg/kg body weight per dose, 0.001 µg/kg body weight-0.01 µg/kg body weight per dose, 0.01 µg/kg body weight-0.1 µg/kg body weight per dose, 0.1 µg/kg body weight-10 µg/kg body weight per dose, 1 µg/kg body weight-100 µg/kg body weight per dose, 100 µg/kg body weight-500 µg/kg body weight per dose, 500 µg/kg body weight per dose-1000 µg/kg body weight per dose, or 1.0 mg/kg body weight per dose-10 mg/kg body weight per dose. However, the particular dose can be determined by a skilled clinician. The disclosed anthranilic amide derivative can be administered in several doses, for example continuously, daily, weekly, or monthly. The administration can concurrent or sequential for other agent.

The mode of administration can be any used in the art. The amount of the disclosed anthranilic amide derivative administered to the subject can be determined by a clinician, and may depend on the particular subject treated. Specific exemplary amounts are provided herein (but the disclosure is not limited to such doses).

A ten percent reduction in one or more sign or symptoms associated with the disease or condition indicates that the treatment is effective.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:
1. A compound of formula:

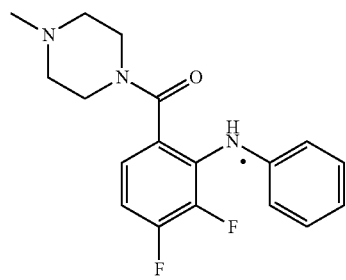 [SMILES: CN1CCN(C(=O)c2ccc(F)c(F)c2Nc2ccccc2)CC1]

or a pharmaceutically acceptable salt thereof.

2. A composition, comprising the compound of claim 1, and a pharmaceutically acceptable carrier.

3. The composition of claim 2, wherein the composition is formulated for oral, intravenous, intradermal, intramuscular, and subcutaneous administration.

4. The composition of claim 3, wherein the composition comprises a product for oral delivery comprising a concentrate, a dried powder, a liquid, a capsule, a pellet, and a pill.

5. A method of inhibiting MEK5 enzymatic activity in a subject comprising:
administering to the subject an effective amount of the compound of claim 1, thereby inhibiting MEK5 enzymatic activity.

* * * * *

UNITED STATES PATENT AND TRADEMARK OFFICE
CERTIFICATE OF CORRECTION

| | |
|---|---|
| PATENT NO. | : 11,465,978 B2 |
| APPLICATION NO. | : 15/021592 |
| DATED | : October 11, 2022 |
| INVENTOR(S) | : Suravi Chakrabarty et al. |

It is certified that error appears in the above-identified patent and that said Letters Patent is hereby corrected as shown below:

In the Specification

In Column 1, Line 46, delete "MAP kinase kinase (MEKK)" and insert -- MAP kinase kinase kinase (MEKK) --.

In Column 1, Line 55, delete "motif" and insert -- motif. --.

In Column 1, Line 59, delete "palyotoxin," and insert -- palytoxin, --.

In Column 5, Line 5, delete "bargraph" and insert -- bar graph --.

In Column 5, Line 13, delete "bargraph" and insert -- bar graph --.

In Column 5, Line 23, delete "R-actin" and insert -- β-actin --.

In Column 7, Line 64, delete "celioblastoma" and insert -- glioblastoma --.

In Column 8, Line 13, delete "craniopharyogioma," and insert -- craniopharyngioma, --.

In Column 8, Line 15, delete "menangioma," and insert -- meningioma, --.

In Column 8, Line 20, delete "actinomyosin" and insert -- actomyosin --.

In Column 8, Line 25, delete "lamelliopodia" and insert -- lamellipodia --.

In Column 8, Line 55, before "the" delete "a".

In Column 13, Line 12, delete "flourine." and insert -- fluorine. --.

In Column 18, Line 1, delete "39." and insert -- 39 (Scheme 3). --.

Signed and Sealed this
Sixth Day of June, 2023

Katherine Kelly Vidal
*Director of the United States Patent and Trademark Office*

In Column 18, Line 7 (approx.), delete "the" and insert -- a --.

In Column 18, Line 8 (approx.), after "chloridinium species" delete "(84)".

In Column 18, Line 14 (approx.), delete "species (Scheme 3)." and insert -- species. --.

In Column 20, Line 16 (approx.), delete "EDCl," and insert -- EDCI, --.

In Column 24, Line 38, delete "iodoanaline" and insert -- iodoaniline --.

In Columns 29-30, Lines 7-9, delete "9e SC-1-72 Ester" and insert -- 9e --.

In Column 38, Line 54, delete "intravitral," and insert -- intravitreal, --.

In Column 38, Line 57, delete "parentral" and insert -- parenteral --.

In Column 40, Line 13, before "also" delete "be".

In Column 41, Lines 5-6, delete "mirocapsules)," and insert -- microcapsules), --.

In Column 41, Line 26, delete "polaxamer" and insert -- poloxamer --.

In Column 41, Line 63, delete "ariations" and insert -- variations --.

In Column 43, Line 42 (approx.), delete "methylpiperazin-l-" and insert -- methylpiperazin-1- --.

In Column 44, Line 23, delete "m." and insert -- μm. --.

In Column 46, Line 26, delete "CDC$_{l3}$):" and insert -- CDCl$_3$): --.

In Column 46, Line 52, delete "R_f_ _0.7" and insert -- Rf 0.7 --.

In Column 46, Line 53, delete "CDC$_{l3}$):" and insert -- CDCl$_3$): --.

In Column 49, Line 24, delete "Rf0.55" and insert -- Rf 0.55 --.

In Column 50, Line 50, delete "CO2." and insert -- CO$_2$. --.

In Column 52, Line 40, delete "(Graph-Pad" and insert -- (GraphPad --.

In Column 52, Line 42, delete "significant" and insert -- significant. --.